US009289456B2

United States Patent
Faria-Waziry et al.

(10) Patent No.: US 9,289,456 B2
(45) Date of Patent: Mar. 22, 2016

(54) MODULATING ONCOLYTIC VESICULAR STOMATITIS VIRUS (VSV) WITH STATINS FOR CANCER TREATMENT

(75) Inventors: Paula A. Faria-Waziry, Fort Lauderdale, FL (US); Luigi X. Cubeddu, Fort Lauderadale, FL (US); Ana Maria Castejon, Fort Lauderdale, FL (US)

(73) Assignee: Nova Southeastern University, Fort Lauderdale, FL (US)

(*) Notice: Subject to any disclaimer, the term of this patent is extended or adjusted under 35 U.S.C. 154(b) by 167 days.

(21) Appl. No.: 13/988,768

(22) PCT Filed: Nov. 22, 2011

(86) PCT No.: PCT/US2011/061920
§ 371 (c)(1),
(2), (4) Date: Jul. 29, 2013

(87) PCT Pub. No.: WO2012/071453
PCT Pub. Date: May 31, 2012

(65) Prior Publication Data
US 2013/0302284 A1    Nov. 14, 2013

Related U.S. Application Data

(60) Provisional application No. 61/252,303, filed on Nov. 22, 2010.

(51) Int. Cl.
| | |
|---|---|
| *A01N 63/00* | (2006.01) |
| *A61K 35/766* | (2015.01) |
| *A61K 31/366* | (2006.01) |
| *A61K 45/06* | (2006.01) |
| *A61K 31/437* | (2006.01) |

(52) U.S. Cl.
CPC ............. *A61K 35/766* (2013.01); *A61K 31/366* (2013.01); *A61K 31/437* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2009/0081161 A1 | 3/2009 | Roberts et al. | |
| 2010/0172877 A1 | 7/2010 | van den Pol | |
| 2010/0303839 A1 | 12/2010 | Bose | |
| 2011/0044952 A1 | 2/2011 | Bell | |
| 2013/0302284 A1* | 11/2013 | Faria-Waziry | A61K 35/766 424/93.6 |

FOREIGN PATENT DOCUMENTS

| | | |
|---|---|---|
| CA | 2818701 | 11/2011 |
| EP | 1932518 | 6/2008 |
| EP | 11843911.6 | 11/2011 |
| WO | 2009/067808 | 6/2009 |

OTHER PUBLICATIONS

Initial Publication with ISR WO 2012071453 published May 31, 2012.
International Preliminary Report for PCT/US2011/061920, filed Nov. 22, 2011.
Written Opinion of the International Search PCT/US2011/061920, filed Nov. 22, 2011.
Libertini et al. Lovastalin enhances the replication of the onolytic adenovirus dl 1520 and its antineoplastic activity against anaplastic thyroid carcinoma cells. Endocrinology. Nov. 2007, vol. 178, No. 11, pp. 5186-5194; col. 1, para 3: p. 5190, col. 2, para 1; Fig 3A, B; p. 5190, col. 2, para 4; p. 5191, col. 2, para 1; Fig 6B.
Enninga et al. Role of nucleoporin induction in releasing am mRNA nuclear export block. Science, 2002, vol. 295, No. 5559, pp. 1523-1525; p. 1524, col. 1, para 1-2.
Coward et al. Statin-induced proinflamatory response in mitogen-activated peripheral blood mononuclear cells through the activation of caspase-1 and IL-18 secretion in monocytes. J Immunl,. 2006, vol. 176, No. 9, pp. 5284-5292; p. 5286, col. 1, para 1; Fig 2B).
Faria et al. VSV disrupts the Rae1/mrnp4 mRNA nuclear export pathway. Mol Cell, 2005, vol. 17, No. 1, pp. 93-102; p. 93, col. 2, para 2-3.
Wang et al. Lovastain, a 3-hydroxy-3-methylglutaryl coenzyme A reductase inhibitor, induces apoptosis and differrentiation in human anaplastic thyroid carcinoma cells. J Clin Endocrinol Metab, Jul. 2003, vol. 88, No. 7, pp. 3021, col. 2, para 7-p. 2023; col. 1, para 2; Fig 1,2.
Joseph et al. The RAF inhibitor PLX4032 inhibits ERK signaling and tumor cell proliferation in a V600E BRAF-selective manner. Proc NatlAcad Sci USA. Aug. 17, 2010 (published online Jul. 28, 2010) vol. 107, No. 33. pp. 14903-14908; p. 14904, col. 2, para 1-2.
European Search Report for EP Application No. 11843911.6 (PCT/US2011/60920) dated Apr. 28, 2014.
Stain Modulation of Oncolytic Vesicular Stomatitis Virus, retrieved from internet on Sep. 4, 2014, Nova Southeastern University.

* cited by examiner

*Primary Examiner* — Michael Burkhart
(74) *Attorney, Agent, or Firm* — Fleit Gibbons Gutman Bongini & Bianco PL; Paul D. Bianco; Katharine Davis

(57) ABSTRACT

In the instant invention, simvastatin (Sim) is used to modulate Vesicular Stomatitis Virus (VSV) infection at the level of viral replication for treatment of cancer. Both lipid-lowering and pleiotropic cellular effects of simvastatin are exploited in this modulation. Simvastatin upregulates the expression of Rae1 and Nup98, therefore altering normal cellular mRNA distribution and reverting VSV's mRNA export block. Furthermore, simvastatin causes redistribution of Flotillin-1, which affects VSV replication/budding. Simvastatin is further used as a neoadjuvant for the selective modulatory control of live VSV oncolytic therapy.

21 Claims, 13 Drawing Sheets

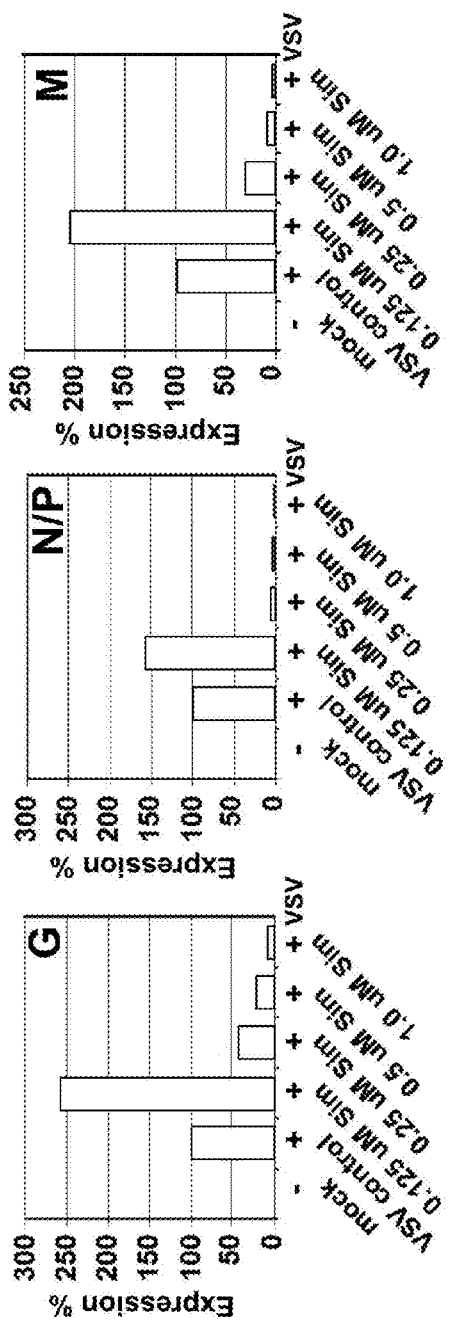
FIG. 3A
FIG. 3B
FIG. 3C
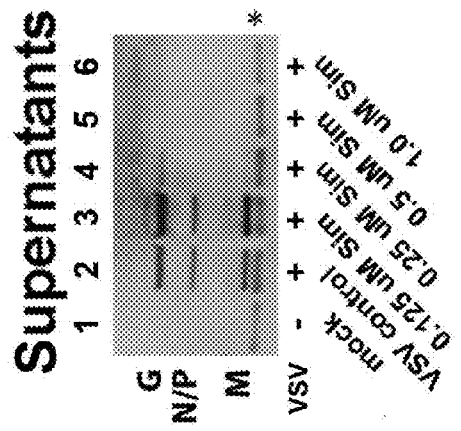
FIG. 4

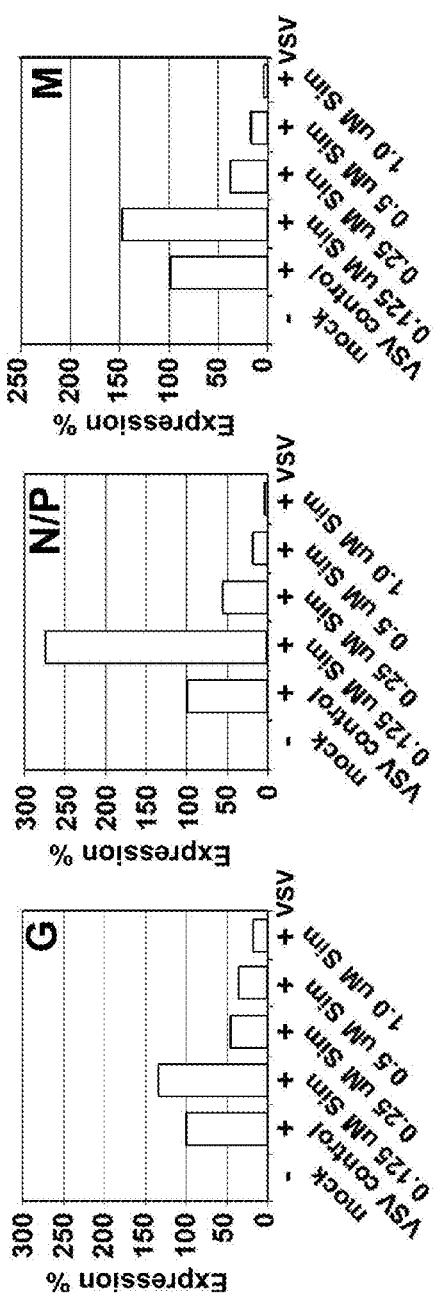
FIG. 5A
FIG. 5B
FIG. 5C
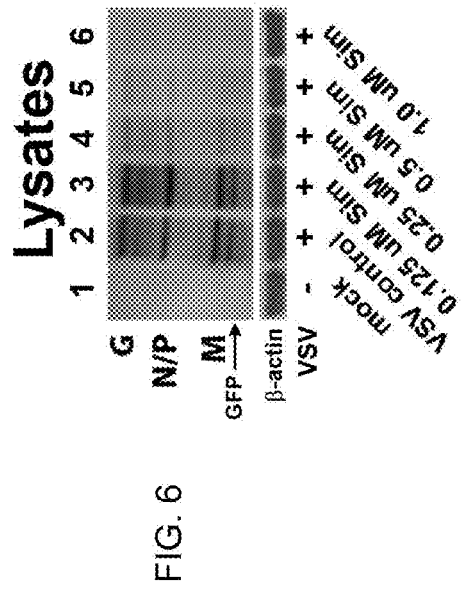
FIG. 6

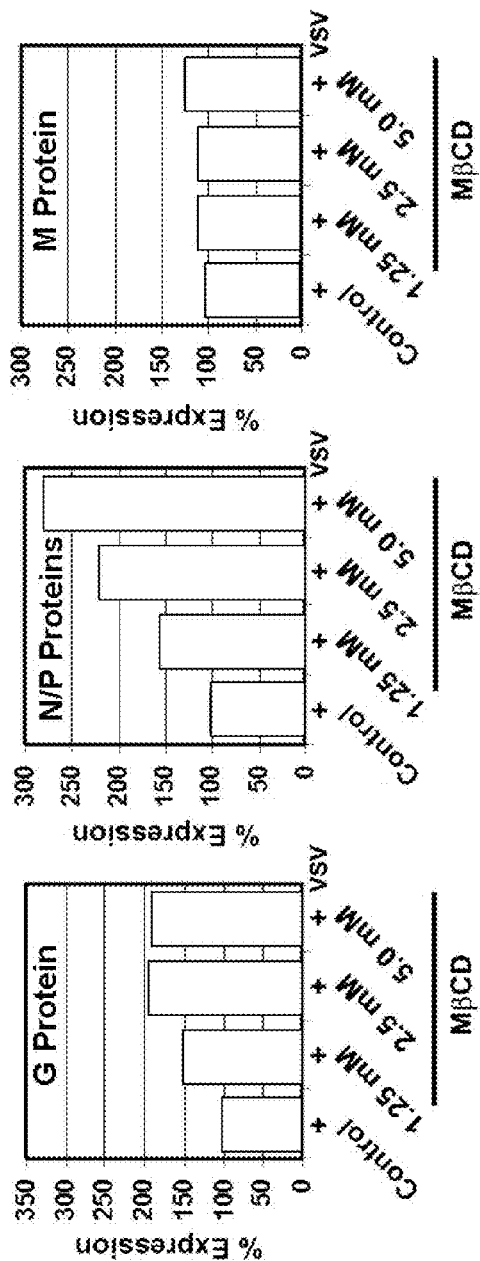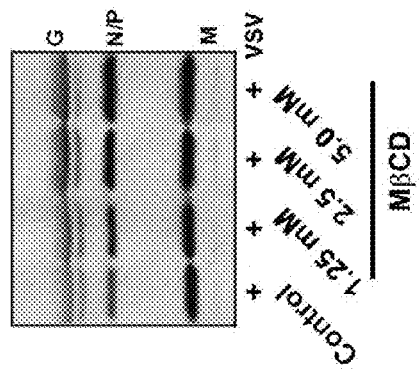
FIG. 9A FIG. 9B FIG. 9C
FIG. 10

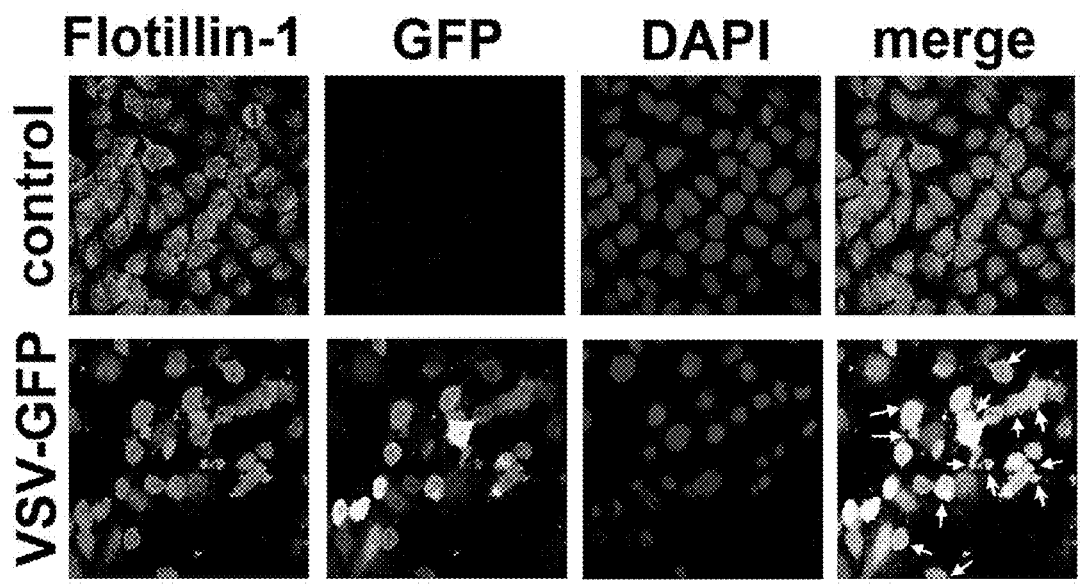
FIG. 13
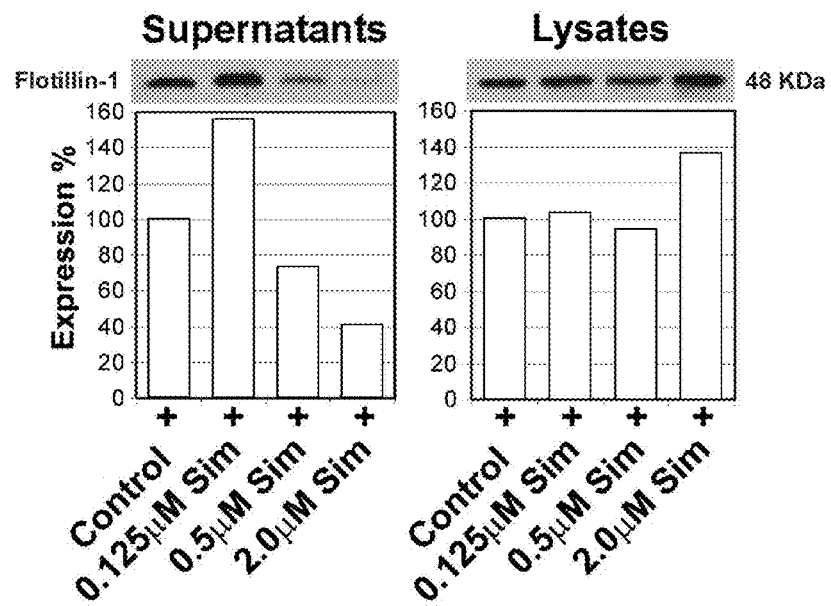

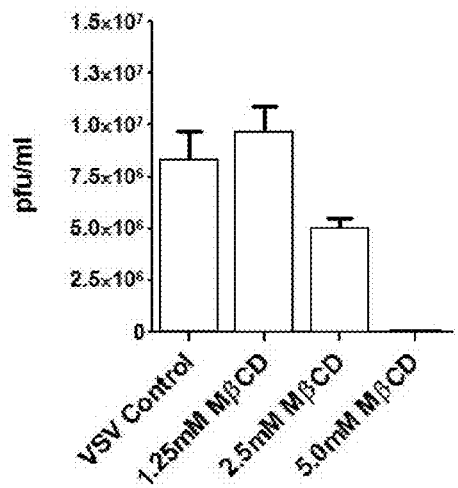
FIG. 17
| Pretreatment | Aver. Titer | Std. Error |
|---|---|---|
| VSV Control | $8.30 \times 10^6$ | $1.40 \times 10^6$ |
| 1.25mM MBCD | $9.65 \times 10^6$ | $1.25 \times 10^6$ |
| 2.5mM MBCD | $5.00 \times 10^6$ | $5.00 \times 10^5$ |
| 5.0mM MBCD | $5.25 \times 10^4$ | $5.50 \times 10^3$ |
FIG. 18
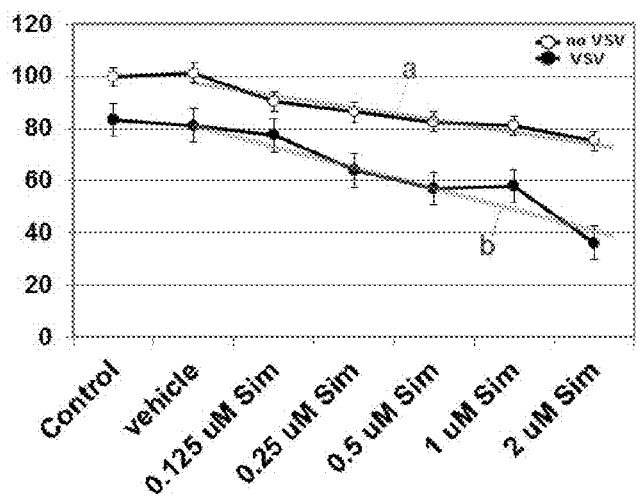

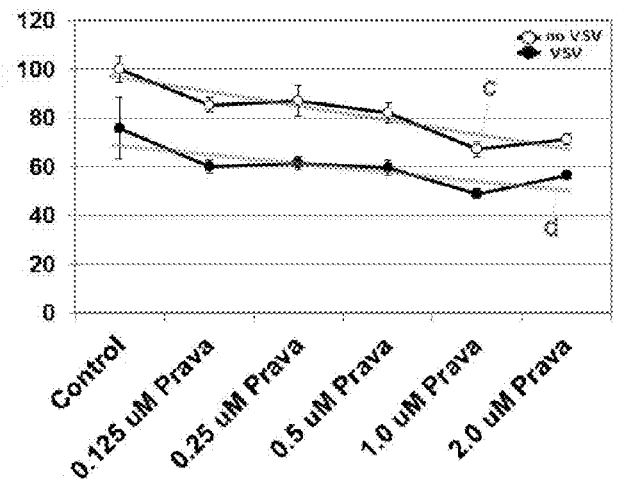
FIG. 19
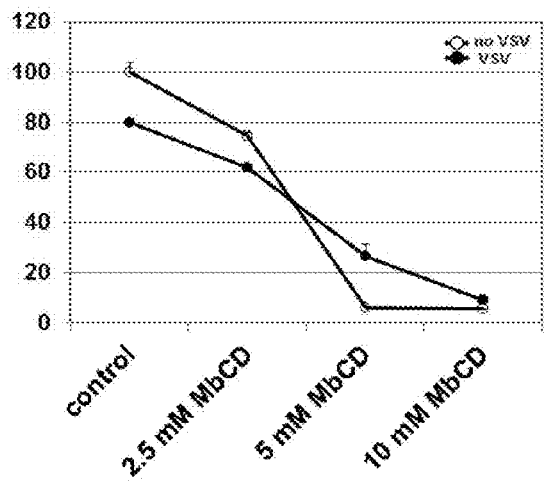
FIG. 20
FIG. 21
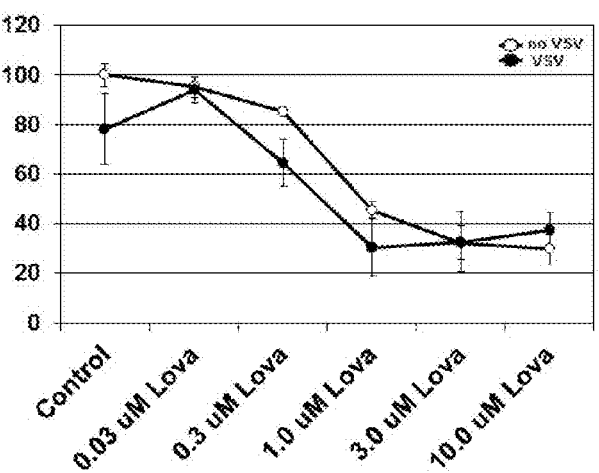

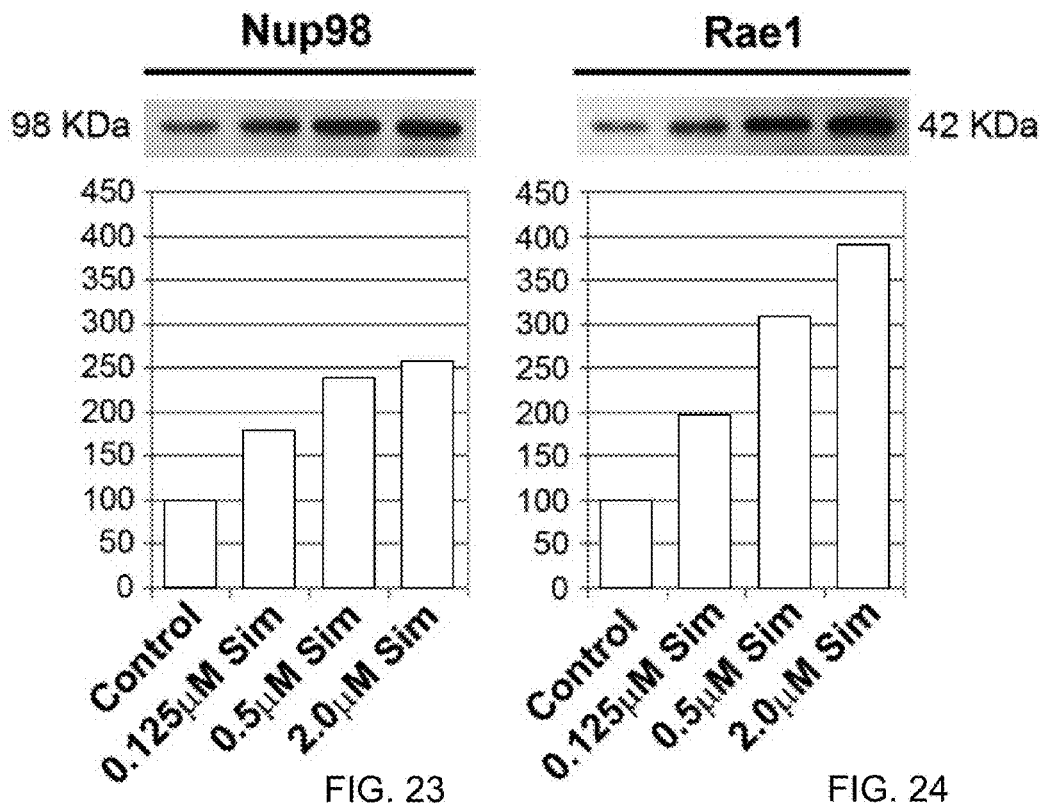
FIG. 23        FIG. 24
FIG. 25        FIG. 26
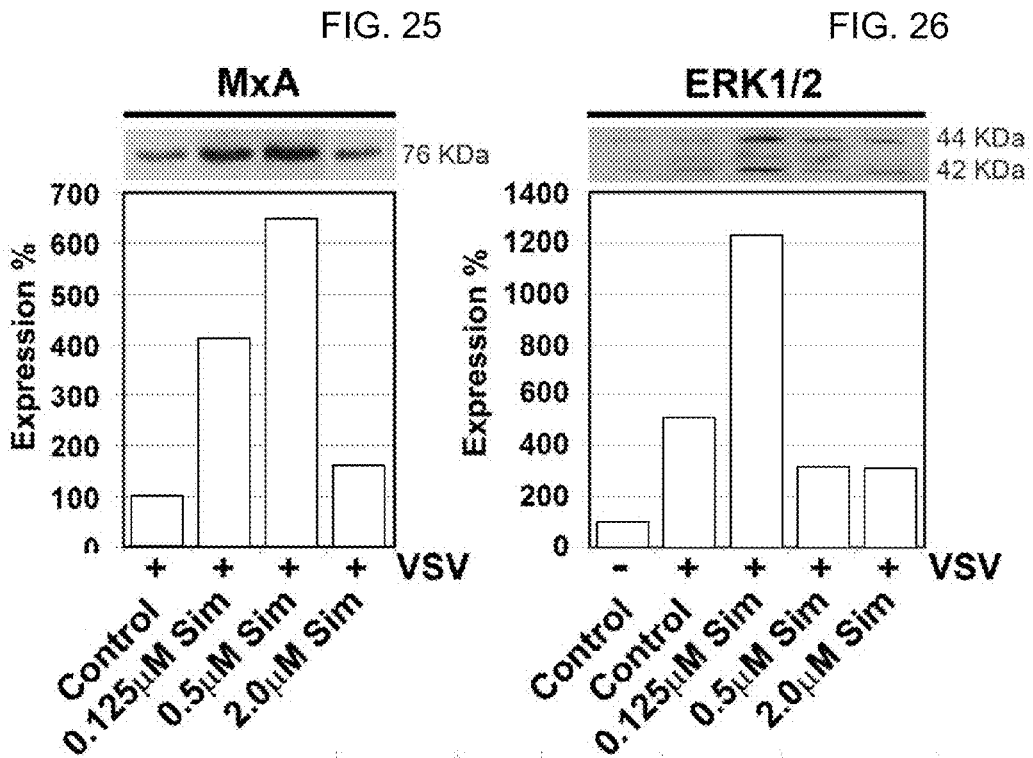

MODULATING ONCOLYTIC VESICULAR STOMATITIS VIRUS (VSV) WITH STATINS FOR CANCER TREATMENT

CROSS REFERENCE TO RELATED APPLICATIONS

This application claims the benefit of related U.S. Provisional Patent Application No. 61/416,080, filed Nov. 22, 2010, the contents of which are incorporated herein by reference.

FIELD OF THE INVENTION

The invention relates to a system and method for statin modulation of oncolytic virus and upregulation of nuclear pore complex proteins and antiviral factors, and in particular, modulation and upregulation using simvastatin.

BACKGROUND OF THE INVENTION

Cancer is the second leading cause of death in the United States and worldwide. Current anticancer treatments have low specificity, affecting cancerous as well as normal cells. New therapeutic approaches, such as the use of viruses with cancer-selective killing properties (oncolytic viruses), are being explored.

In the United States, the number of cancer deaths among people younger than 85, surpasses the number of deaths due to heart disease (1) (Numbers in parentheses refer to the Bibliography which follows this section). Currently, there are many anti-cancer treatments, however, cure or long term remission and clinical success have come with significant toxic side effects, acute and chronic morbidity. The low efficacy attributed to anti-cancer treatment creates an urgent need for innovative therapeutic strategies.

One such strategy known as virotherapy, utilizes live viruses that have selective cancer-killing properties. However, oncolytic virotherapy is in its infancy and must overcome several obstacles before rendered as safe and effective for the management of cancer patients.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 CFR §1.56(a) exists.

BIBLIOGRAPHY

1. Jemal A, Murray T, Ward E, Samuels A, Tiwari R C, Ghafoor A, Feuer E J, & Thun M J (2005) *CA Cancer J Clin* 55, 10-30.
2. Kelly E J, Nace R, Barber G N, & Russell S J (2009) *J. Virol.*
3. Saloura V, Wang L C, Fridlender Z G, Sun J, Cheng G, Kapoor V, Sterman D H, Harty R N, Okumura A, Barber G N, et al. (2009) *Hum Gene Ther.*
4. Pincetic A & Leis J (2009) *Adv Virol* 2009, 6239691-6239699.
5. Obuchi M, Fernandez M, & Barber G N (2003) *J Virol* 77, 8843-8856.
6. Ahmed M, McKenzie M O, Puckett S, Hojnacki M, Poliquin L, & Lyles D S (2003) *J Virol* 77, 4646-4657.
7. Stojdl D F, Lichty B, Knowles S, Marius R, Atkins H, Sonenberg N, & Bell J C (2000) *Nat Med* 6, 821-825.
8. Noser J A, Mael A A, Sakuma R, Ohmine S, Marcato P, Lee P W, & Ikeda Y (2007) *Mol Ther* 15, 1531-1536.
9. Barber G N (2004) *Viral Immunol* 17, 516-527.
10. Fernandez M, Porosnicu M, Markovic D, & Barber G N (2002) *J Virol* 76, 895-904.
11. Gustin K E (2003) *Virus Res* 95, 35-44.
12. von Kobbe C, van Deursen J M, Rodrigues J P, Sitterlin D, Bachi A, Wu X, Wilm M, Carmo-Fonseca M, & Izaurralde E (2000) *Mol Cell* 6, 1243-1252.
13. Faria P A, Chakraborty P, Levay A, Barber G N, Ezelle H J, Enninga J, Arana C, van Deursen J, & Fontoura B M (2005) *Mol Cell* 17, 93-102.
14. Tran E J & Wente S R (2006) *Cell* 125, 1041-1053.
15. Terry L J, Shows E B, & Wente S R (2007) *Science* 318, 1412-1416.
16. Izaurralde E (2002) *Eur J Cell Biol* 81, 577-584.
17. Enning a J, Levy D E, Blobel G, & Fontoura B M (2002) *Science* 295, 1523-1525.
18. Chen J, Huang S, & Chen Z (2010) *J Gen Virol.*
19. Satterly N, Tsai P L, van Deursen J, Nussenzveig D R, Wang Y, Faria P A, Levay A, Levy D E, & Fontoura B M (2007) *Proc Natl Acad Sci USA* 104, 1853-1858.
20. Castello A, Izquierdo J M, Welnowska E, & Carrasco L (2009) *J Cell Sci* 122, 3799-3809.
21. Moore M, Schaack J, Baim S B, Morimoto R I, & Shenk T (1987) *Mol Cell Biol* 7, 4505-4512.
22. Chung K M, Lee J, Kim J E, Song O K, Cho S, Lim J, Seedorf M, Hahm B, & Jang S K (2000) *J Virol* 74, 5233-5241.
23. Ebina H, Aoki J, Hatta S, Yoshida T, & Koyanagi Y (2004) *Microbes Infect* 6, 715-724.
24. Pryor M J, Rawlinson S M, Butcher R E, Barton C L, Waterhouse T A, Vasudevan S G, Bardin P G, Wright P J, Jans D A, & Davidson A D (2007) *Traffic* 8, 795-807.
25. Park N, Katikaneni P, Skern T, & Gustin K E (2008) *J Virol* 82, 1647-1655.
26. Alvisi G, Rawlinson S M, Ghildyal R, Ripalti A, & Jans D A (2008) *Biochim Biophys Acta* 1784, 213-227.
27. Blevins M B, Smith A M, Phillips E M, & Powers M A (2003) *J Biol Chem* 278, 20979-20988.
28. Xu S & Powers M A (2009) *Semin Cell Dev Biol* 20, 620-630.
29. Sun Y & Guo H C (2008) *Protein Sci* 17, 494-505.
30. Chilton R J (2003) *J Am Osteopath Assoc* 103, S12-17.
31. Amet T, Nonaka M, Dewan M Z, Saitoh Y, Qi X, Ichinose S, Yamamoto N, & Yamaoka S (2008) *Microbes Infect* 10, 471-480.
32. del Real G, Jimenez-Baranda S, Mira E, Lacalle R A, Lucas P, Gomez-Mouton C, Alegret M, Pena J M, Rodriguez-Zapata M, Alvarez-Mon M, et al. (2004) *J Exp Med* 200, 541-547.
33. Liu Z, Guo Z, Wang G, Zhang D, He H, Li G, Liu Y, Higgins D, Walsh A, Shanahan-Prendergast L, et al. (2009) *Eur J Pharm Sci* 38, 215-223.
34. Liu S, Rodriguez A V, & Tosteson M T (2006) *Biochem Biophys Res Commun* 347, 51-59.
35. Delang L, Paeshuyse J, Vliegen I, Leyssen P, Obeid S, Durantel D, Zoulim F, Op de Beeck A, & Neyts J (2009) *Hepatology* 50, 6-16.
36. Ikeda M & Kato N (2007) *J Pharmacol Sci* 105, 145-150.
37. Bader T & Korba B (2010) *Antiviral Res* 86, 241-245.
38. Potena L, Frascaroli G, Grigioni F, Lazzarotto T, Magnani G, Tomasi L, Coccolo F, Gabrielli L, Magelli C, Landini M P, et al. (2004) *Circulation* 109, 532-536.
39. Gower T L & Graham B S (2001) *Antimicrob Agents Chemother* 45, 1231-1237.

40. Rothwell C, Lebreton A, Young Ng C, Lim J Y, Liu W, Vasudevan S, Labow M, Gu F, & Gaither L A (2009) *Virology* 389, 8-19.
41. Malvoisin E & Wild F (1990) *Biochim Biophys Acta* 1042, 359-364.
42. Libertini S, Iacuzzo I, Ferraro A, Vitale M, Bifulco M, Fusco A, & Portella G (2007) *Endocrinology* 148, 5186-5194.
43. Ye J, Wang C, Sumpter R, Jr., Brown M S, Goldstein J L, & Gale M, Jr. (2003) *Proc Natl Acad Sci USA* 100, 15865-15870.
44. Gilbert C, Bergeron M, Methot S, Giguere J F, & Tremblay M J (2005) *Viral Immunol* 18, 474-489.
45. Reichelt M, Stertz S, Krijnse-Locker J, Haller O, & Kochs G (2004) *Traffic* 5, 772-784.
46. Frick M, Bright N A, Riento K, Bray A, Merrified C, & Nichols B J (2007) *Curr Biol* 17, 1151-1156.
47. Coward W R, Marei A, Yang A, Vasa-Nicotera M M, & Chow S C (2006) *J Immunol* 176, 5284-5292.
48. Scholl F A, Dumesic P A, & Khavari P A (2005) *Cancer Lett* 230, 1-5.
49. Bos J L (1989) *Cancer Res* 49, 4682-4689.
50. He Y P, Zhao L Y, Zheng Q S, Liu S W, Zhao X Y, Lu X L, Niu X L, & Li X (2008) *Mol Cell Biochem* 317, 33-41.
51. Ikeda M, Abe K, Yamada M, Dansako H, Naka K, & Kato N (2006) *Hepatology* 44, 117-125.
52. Bonnet F, Aurillac-Lavignolle V, Breilh D, Thiebaut R, Peuchant E, Bernard N, Lacoste D, Dabis F, Beylot J, Chene G, et al. (2007) *HIV Clin Trials* 8, 53-60.
53. Medina R J, O'Neill C L, Devine A B, Gardiner T A, & Stitt A W (2008) *PLoS One* 3, e2584.
54. Joseph E W, Pratilas C A, Poulikakos P I, Tadi M, Wang W, Taylor B S, Halilovic E, Persaud Y, Xing F, Viale A, et al. (2010) *Proc Natl Acad Sci USA* 107, 14903-14908.
55. Park I H, Kim J Y, Choi J Y, & Han J Y (2010) *Invest New Drugs*.
56. Hwang K E, Na K S, Park D S, Choi K H, Kim B R, Shim H, Jeong E T, & Kim H R (2010) *Invest New Drugs*.
57. Ghavami S, Mutawe M M, Hauff K, Stelmack G L, Schaafsma D, Sharma P, McNeill K D, Hynes T S, Kung S K, Unruh H, et al. (2010) *Biochim Biophys Acta* 1803, 452-467.
58. Bababeygy S R, Polevaya N V, Youssef S, Sun A, Xiong A, Prugpichailers T, Veeravagu A, Hou L C, Steinman L, & Tse V (2009) *Anticancer Res* 29, 4901-4908.
59. Lee S K, Kim Y C, Song S B, & Kim Y S (2010) *Biochem Biophys Res Commun* 391, 1592-1597.
60. Minichsdorfer C & Hohenegger M (2009) *Br J Pharmacol* 157, 1278-1290.
61. Kato S, Smalley S, Sadarangani A, Chen-Lin K, Oliva B, Branes J, Carvajal J, Gejman R, Owen G I, & Cuello M (2009) *J Cell Mol. Med.*

SUMMARY OF THE INVENTION

In accordance with the disclosure, a method of treating cancer in a patient comprises administering to the patient having cancer an effective amount of an oncolytic virus and modulating virus replication with a statin. In various embodiments, the statin modulates virus replication by upregulating nuclear pore complex antiviral factors; the nuclear pore complex antiviral factors are Rae1 and Nup98; the oncolytic virus is Vesicular Stomatitis Virus; and the statin is simvastatin.

In another embodiment, a combination cancer treatment therapy comprises an effective amount of Vesicular Stomatitis Virus (VSV), and an effective amount of simvastatin (Sim), wherein the effective amount of VSV and the effective amount of Sim synergistically enhance cancer-cell apoptosis. In further embodiment, the Sim modulates the virus by upregulating nuclear pore complex antiviral factors; the nuclear pore complex antiviral factors are Rae1 and Nup98; and the patient is first pretreated with said statin and then administered an effective amount of an oncolytic virus.

In a yet further embodiment, a cancer treatment therapy comprises administering a statin at a first dosage level to cancer cells of the patient; infecting cancer cells of the patient with Vesicular Stomatitis Virus (VSV) between 0 and 24 hours after administering the statin, growth of VSV and associated oncolysis thereby enhanced by the statin. Embodiments include said statin is selected from the group consisting of a lipophilic statin, simvastatin; said statin is simvastatin, and is administered at a concentration of between about 0.01 and about 0.175 μM; said statin is simvastatin, and is administered at a concentration of about 0.125 μM; infection is with VSV at a Multiplicity of Infection of about 0.01 to 2.0; infection is with VSV at a Multiplicity of Infection of about 1.0.

The therapy, in another embodiment, further includes the step of administering a statin at a second, higher dosage level, to cells of the patient, thereby causing the statin to exhibit an antiviral effect on the VSV. Other embodiments include the higher dosage level being about 0.25 μM or higher; further including the step, a substantial time after administering the statin, of administering to the patient a different anticancer therapeutic substance; the different anticancer therapeutic substance is an inhibitor of the RAS/Raf/ERK pathway; the different anticancer therapeutic substance is administered at least about 4 hours after the statin; and, the statin is simvastatin and the different anticancer therapeutic substance is PLX4032.

BRIEF DESCRIPTION OF THE DRAWINGS

A more complete understanding of the present invention, and the attendant advantages and features thereof, will be more readily understood by reference to the following detailed description when considered in conjunction with the accompanying drawings, described as follows.

FIG. 2 illustrates the Nuclear Pore Complex (NPC) and viruses that take-over NPC functions. The NPC is a massive structure (~125 MDa) embedded in the double bilayer of the nuclear membrane. Illustrated on the left are the viruses known to import/export their contents via kariopherins (transportins) that interact with nup98. This panel of viruses coincides with the ones observed to be affected by statin drugs. On the right are viruses that disrupt or downregulate Nups. VSV is a prototype virus with a well-defined mechanism that directly blocks mRNA export via interactions with Rae1/Nup98.

FIG. 1 illustrates the life cycle of VSV. Each VSV virion has one copy of a 11.1 Kb (–)ssRNA genome. The genome is composed of 5 genes that encode: Nucleocapsid (N), Phosphoprotein (P), Matrix (M), envelope Glycoprotein (G), and Polymerase, or "Large" protein (L). VSV can accommodate foreign genes in its genome (ie. Green Fluorescent Protein (GFP)). (1) Attachment of VSV to host cell membrane. (2) Receptor-mediated endocytosis of viral particle. (3) Acidification of vesicle with subsequent membrane fusion and release of VSV genome into the cytoplasm. (4) Translation of viral proteins. (5) The levels of protein expression depend on how far each encoding gene is from the 3' end of the polycistronic genomic (–)RNA. (6) Viral assembly and budding at the cell membrane, where G and M proteins aggregate at specific sites to facilitate viral exit.

FIGS. 3A-3C, 4, 5A-5C, and 6 illustrate data with respect to simvastatin pre-treatment altering VSV protein expression in HeLa cells. HeLa cells were pre-treated with the indicated concentrations of simvastatin for 8 h prior to infection with VSV-GFP, MOI of 1.0, for 16 h.

Detection of viral proteins are shown by immunoblot assays performed with anti-VSV-GFP antibodies. FIGS. 3A-3C and 4 and FIGS. 5A-5C and 6: Immunoblot of VSV proteins from samples of supernatants and cell lysates, respectively. Detectable VSV protein bands are indicated by G, Glycoprotein, N/P, Nucleocaspid/Polymerase, and M, Matrix protein. In the supernatants, a non-specific crossreacting band is indicated by an asterisk and served as loading control. In the lysates, protein bands were normalized against β-actin expression levels. Also in cell lysates, an extra VSV band is detected, corresponding to the expression of GFP protein. Corresponding bar graphs were normalized to the loading controls and to VSV control infections, arbitrarily set to 100% (FIG. 4, lane 2; FIG. 6, lane2). It should be understood that while infection was effective with a MOI of about 1.0, in accordance with the disclosure, a lower or higher MOI may be used, for example advantageously in the range of 0.01 to 2.0, although smaller or higher ranges may still be used effectively.

FIGS. 9A-9C, 10, 11A-11C, and 12 illustrate Methyl-β-Cyclodextrin pre-treatment enhancement of VSV protein expression in HeLa cells. HeLa cells were pre-treated with the indicated concentrations of MβCD for 45 min. prior to infection with VSV-GFP at MOI of 1.0, for 16 h. Detection of viral proteins are shown by immunoblot assays performed with anti-VSV-GFP antibodies. FIGS. 9A-9C, 10, 11A-11C, and 12: Immunoblot of VSV proteins from samples of cell lysates and supernatants, respectively. Detectable VSV protein bands are indicated by G, Glycoprotein, N/P, Nucleocaspid/Polymerase, and M, Matrix protein. Corresponding bar graphs were normalized to the loading controls and to VSV control infections, arbitrarily set to 100%.

FIGS. 13 and 14A-14B illustrate a profile of lipid raft protein Flotillin-1. FIG. 13-VSV co-localizing with Flotillin-1. HeLa cells were either infected (VSV-GFP) or not (control) at MOI of 1.0 O/N. Cells were then fixed, permeabilized and immunostained against Flotillin-1. Control cells show normal uniform distribution of Flotillin-1 across the cytoplasm. Infected cells show re-distribution of Flotillin-1 towards regions of vesicle-like structures with high viral content (merge/arrows); FIGS. 14A-14B—Simvastatin shifts Flotillin-1 distribution between supernatant and cell lysates. Cells were pretreated with the corresponding concentrations of simvastatin for 8 hrs, then infected with VSV-GFP at MOI 1.0 for 16 hrs. WBs show levels of Flotillin-1 from supernatants and cell lysates corresponding to each pretreatment condition. Bar graphs indicate quantitation of WB bands. At low concentration of 0.125 μM simvastatin, Flotillin-1 levels are overall increased and unevenly distributed towards the supernatant. At higher concentrations, there is a shift on Flotillin-1 distribution towards cell lysates.

FIGS. 15-17 illustrate cholesterol-lowering drugs pretreatments of Hela cells and attenuation of viral titers. HeLa cells were pretreated with the indicated concentrations of either simvastatin, or pravastatin for 24 h prior to VSV-GFP infection at MOI of 1.0. VSV infections proceeded for 16 h. Experiments conducted using MβCD, the pretreatment time was 45 minutes, followed by 16 h VSV infection at MOI of 1.0. Samples of supernatants (cell culture media) containing progeny VSV were collected and assayed for viral titers. FIG. 15—Titers of supernatants of HeLa cells pretreated with simvastatin ($p<0.0001$). FIG. 16—Titers of supernatants of HeLa cells pretreated with Pravastatin ($p=0.4644$). FIG. 17—Titers of supernatants of HeLa cells pretreated with methyl-β-cyclodextrin ($p=0.0076$).

FIGS. 18-21 illustrate a viability of HeLa cells pretreated with simvastatin, pravastatin, or MβCD and infected (or not) with VSV-GFP. FIG. 18—Simvastatin Pretreatment: In one group of experiments, HeLa cells were pretreated with simvastatin 0.125-2 μM for 8 hrs and then infected with VSV-GFP, MOI of 1.0, for 16 h (filled circles). In the other group, the pretreatment with 0.125-2 μM simvastatin for 8 hrs was not followed by VSV infection (open circles). Relative trend of cell survival is represented by the slopes derived from each group (a: m=−6.54, and b: m=−10.46). FIG. 19-Pravastatin Pretreatment: HeLa cells were pretreated as in FIG. 18, substituting simvastatin for pravastatin. Open circles: no VSV. Closed circles: VSV infections. FIG. 20—MβCD Pretreatment: Cells were pretreated for 45 min with the indicated concentrations of MβCD, then infected (closed circles) or not (open circles) with VSV-GFP for 16 hrs. FIG. 21—Lovastatin pretreatment: HeLa cells were pretreated as in FIG. 18, substituting simvastatin for lovastatin. Open circles: no VSV. Closed circles: VSV infections.

FIGS. 23-24 illustrate simvastatin treatment increasing protein expression of nuclear mRNA export factor Rae1 and nucleoporin Nup98. HeLa cells were treated with the indicated concentrations of Sim for 24 hrs. Detection of proteins from cell lysates are shown by immunoblot assays performed with anti-Nup98 and anti-Rae1 antibodies.

FIGS. 25-26 illustrate simvastatin treatment modulating protein expression of MxA and ERK1/2. HeLa cells were treated with the indicated concentrations of Sim for 24 hrs. Detection of proteins from cell lysates are shown by immunoblot assays performed with anti-MxA and anti-ERK1/2 antibodies.

DETAILED DESCRIPTION OF THE INVENTION

Figure 1:
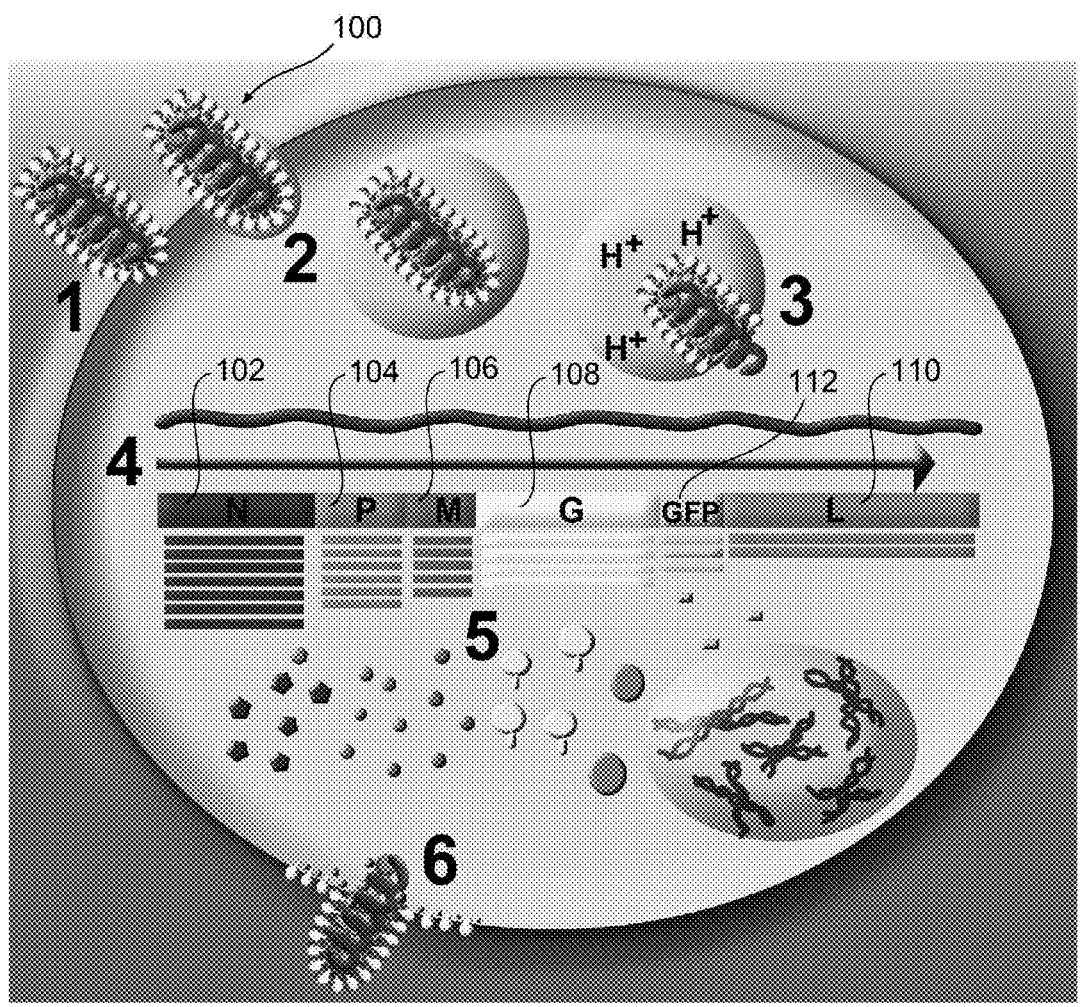
FIGS. 1 and 2 represent current theories regarding the action and life cycle of Vesicular Stomatitis Virus (VSV), although the accuracy of these theories is not essential in order to carry out the instant disclosure.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

Vesicular Stomatitis Virus (VSV) is relatively non-pathogenic to humans, and preferentially replicates in cancer cells, due to these cells' defects on interferon (IFN) and MAPK cellular innate immunity (RAS/Raf/ERK and MxA) signaling pathway. In accordance with the disclosure, normal cells tend to recover quickly from VSV infections, however, there are risks associated with uncontrolled infections and neurotoxicity.

In accordance with the disclosure, the mechanism by which VSV causes cytopathic effects is mainly by interacting with the Nuclear Pore Complex (NPC) mRNA export factors Rae1 and Nup98, blocking mRNA nuclear export, and by arresting cell division. The instant disclosure uncovers a class of drugs capable of controlling VSV replication/infection and simultaneously protecting healthy cells, thereby enhancing VSV as an oncolytic therapy. More particularly, statins, the extensively used cholesterol-lowering drugs, exert other actions, known as pleiotropic effects. Among them, statins are shown to (a) induce cytoprotection on normal cells; (b) inhibit the replication of viruses, such as HIV, HCV, polio and influenza; and (c) to increase the replication of oncolytic adenovirus.

At the cell surface, statins alter the composition of lipid rafts, which exert important functions in viral replication/budding. Intracellularly, statins modulate the expression of interferon, as well as downstream signaling events, such as MAPK (RAS/Raf/ERK) pathway. Here, we have investigated the actions of statins (simvastatin, lovastatin and pravastatin), as well as Methyl-β-cyclodextrin (MβCD, a cholesterol-sequestering drug) on VSV infection, lipid raft integrity, and protein levels of Rae1, Nup98, ERK1/2, and MxA.

Overview

Methods:

HeLa cells were exposed to different concentrations of statins or MβCD. Cells were infected with VSV-GFP. Protein expression was analyzed by immunoblots. Viral titers were obtained from culture supernatants. In situ hybridization of mRNA was performed and imaging analysis was done using confocal microscopy. Cell viability was determined by MTT assays.

Results:

Low concentration (0.125 µM) of simvastatin or MβCD treatment enhanced VSV replication. Higher doses of simvastatin (0.25-4 µM) caused a concentration-dependent antiviral effect. Simvastatin increased the protein levels of Rae1 and Nup98, and reversed the VSV-induced mRNA export block in a dose-dependent manner. Protein levels of lipid raft marker Flotillin-1, as well as levels of ERK1/2, and MxA were also altered by simvastatin treatment. In accordance with the disclosure, low concentrations are between 0.01 and less than 0.25 µM, and higher concentrations between about 0.5 and about 4.0 µM.

Conclusions:

Simvastatin appears to modulate VSV infection at the level of viral replication. Both lipid-lowering and pleiotropic cellular effects of simvastatin may be important for such modulation. Simvastatin appears to modulate the expression of Rae1 and Nup98, therefore altering cellular mRNA distribution and reverting VSV's mRNA export block. Furthermore, simvastatin caused redistribution of Flotillin-1, a lipid raft marker, which may be important for VSV replication/budding. It is disclosed that simvastatin may advantageously be used as a neoadjuvant for the selective modulatory control of live VSV oncolytic therapy.

Two of the major barriers of viral oncolysis are: (a) the innate immune system, which can rapidly destroy oncolytic viruses, and (b) the risk of uncontrollable systemic viral infections, which can cause neurotoxicity (2, 3). Overcoming there barriers requires the use of drugs capable of minimizing infectivity to normal cells and/or enhancing the viral oncolytic potency.

Viral infections in general, persistently threaten human health, and are difficult to control. A classical approach towards the development of antiviral drugs is the discovery of agents that directly bind/inhibit viral particles. These drugs tend to have small and specific ranges of drug action, and are further limited by the fact that many viruses mutate frequently, quickly falling out of interacting range. An approach disclosed herein to antiviral drug development, is to target strategic antiviral host factors, and not viral particles directly. When drugs are directed towards cellular components, they can be effective against several unrelated viruses, since those need common host cellular factors for proper replication and budding (4). This approach enables the development of broad range antiviral agents, which may be useful not only towards effective viral oncolysis, but also as mainstream antiviral therapy.

The disclosure details an investigation of the oncolytic properties of Vesicular Stomatitis Virus (VSV), as well as drugs capable of controlling VSV infection. VSV is oncolytic in nature, meaning that it preferentially kills cancer cells (5). Importantly, VSV's preferential replication in cancer cells is due to these cells' flaws in interferon (IFN) antiviral immune pathways (5-7). Such defects involve flawed induction of RAS/Raf/ERK signaling, which in turn upregulate antiviral MxA protein. It has been suggested that a cellular compensation for such flaws involves constitutive activation of RAS/Raf/ERK signaling pathway. The later promotes enhanced VSV replication, as well as the promotion of cell division and survival (8). Approximately 70% of all tumors, and in particular types that are persistently resistant to conventional therapy, have constitutive upregulation of RAS/Raf/ERK pathway proteins. Moreover, it is known that this same defective pathway favors robust replication of VSV in particular, therefore allowing for increased viral oncolysis (8).

VSV is advantageously used in clinical trials as a cancer-selective, replication-competent therapeutic vector (9, 10). It exclusively replicates in the cytoplasm, and not in the nucleus of infected cells, therefore rendering it advantageous over other oncolytic viruses. VSV's genetic material does not become integrated into the host's chromosomes, avoiding controversial risks of oncogenic nature. VSV is relatively non-pathogenic to humans; nevertheless, it is capable of finding and destroying localized inaccessible tumors, such as brain cancers, as well as dispersed metastatic cells, considered difficult to detect/treat with available therapeutic means.

With reference to FIG. 1, VSV 100 is an enveloped, negative-strand RNA virus that encodes its own set of enzymes for transcription and replication. The genome of wild-type VSV is composed of 5 genes that encode proteins: Nucleocapsid (N) 102, Phosphoprotein (P) 104, Matrix (M) 106, envelope Glycoprotein (G) 108, and Polymerase, or "Large" protein (L) 110. The manipulation of VSV's genome is easily accomplished, and constructed mutants are capable of expressing foreign genes, as for example a marker Green Fluorescent Protein (GFP) 112.

VSV induces a variety of cytopathic effects in the cells it infects, including morphological changes, cell rounding and apoptosis (11, 12). Most of VSV's cytopathic effects are caused by M protein, which is responsible for blocking mRNA nuclear export, inhibiting host protein synthesis, which favors VSV's own cytoplasmic replication and viability (12, 13).

Figure 2:
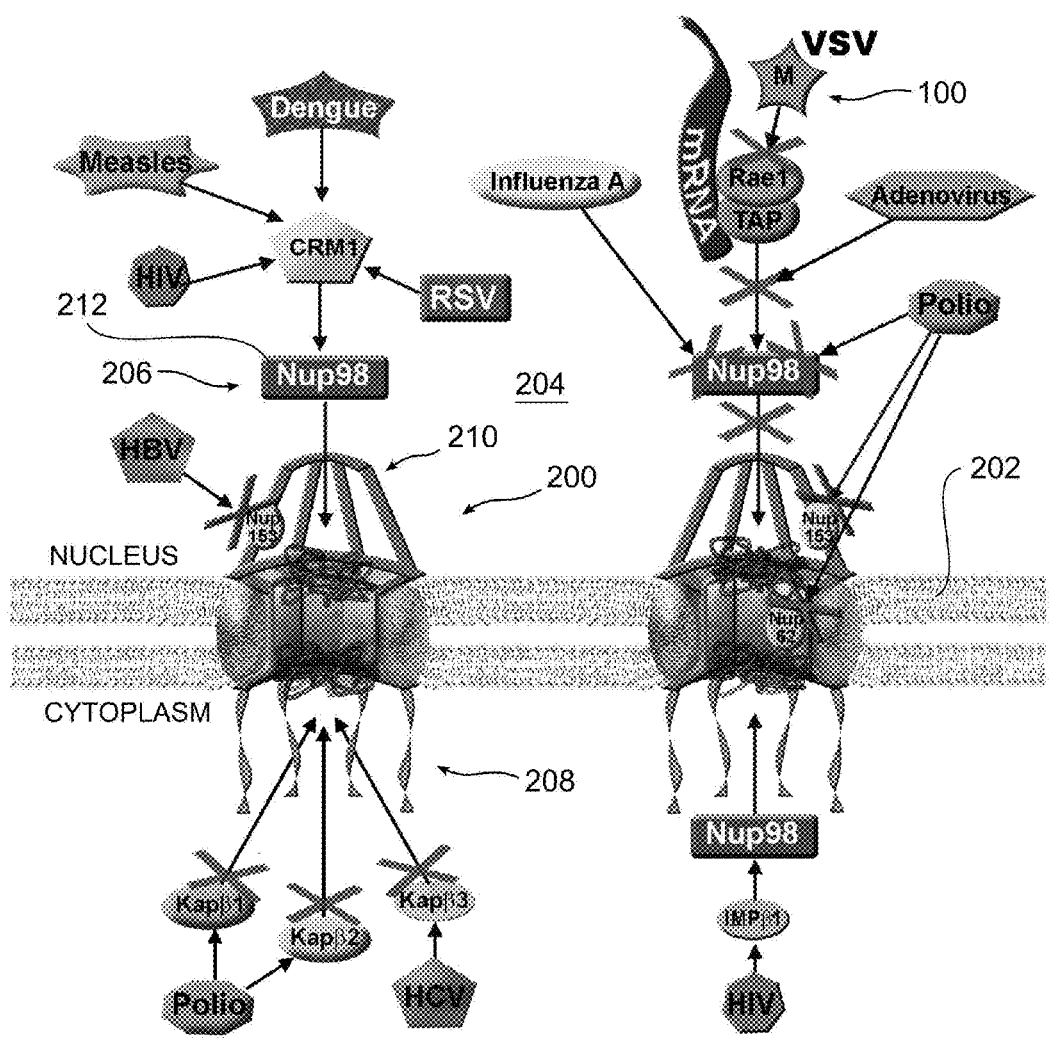

Viruses in general need to use the host cellular machinery in order to replicate, therefore they must take-over primary cell functions. The most striking characteristic of eukaryotic cells is the presence of nuclei that compartmentalize the processes of transcription and translation. With reference to FIG. 2, a key regulator of such compartmentalization is the Nuclear pore Complex (NPC) 200. NPCs form openings in the nuclear envelope 202 allowing translocation of cargos, and regulate all traffic of proteins, nucleic acids and viral particles into and out of the nucleus (14) 204. NPCs 200 are large structures composed of approximately 30 different proteins called nucleoporins (Nups) 206. NPCs have eight-fold symmetry, and each Nup is present in 8-48 copies, forming a complex of approximately 125 MDa. On the cytoplasmic side of the NPC, eight fibers 208 extrude from a central ring-like structure, which is embedded in the nuclear envelope. On the intranuclear side, 8 fibers form the nuclear basket (15) 210. The nuclear transport machinery is advantageously used in accordance with the disclosure to modulate cellular genetic programs involved in antiviral and anticancer strategies. A common feature of viruses that infect non-dividing cells is that they either penetrate the nuclear envelope through the NPCs, or take over NPC functions in order to favor viral replication, as shown in FIG. 2.

In accordance with the disclosure, VSV takes over cellular function as follows: VSV M protein causes the blockage of mRNA export by interacting with the mRNA Export factor 1 (Rae1, also known as mrnp41) (13). Rae1 is a nucleoporin (Nup) responsible for the export of hnRNPs through the central channel of the NPC via interactions with Nup98 (16) 212. Upregulation of Rae1, or of Nup98, can revert the VSV mRNA export block, and therefore restore normal mRNA export, which leads to a fast cellular innate immune response and recovery from infection (13, 17). As is the case for other oncolytic viruses, the use of VSV as a mainstream systemic oncolytic agent presents the risks of unwanted infections of healthy cells. This disclosure presents a class of drugs which protect healthy cells, and allow control of VSV infection/replication on cancerous cells.

FIG. 2 illustrates viruses interacting with NPC 200 components. For example, Viruses known to downregulate Nup98 and block mRNA export are influenza (18, 19) and poliovirus (20). Adenovirus blocks mRNA export (21), but has not been shown to degrade Nups. Other Nups degraded by viruses are Nup153 by HBV and polio; Nup62 and Kapβ2 by polio (20); and Kapβ3 by HCV (22). Viruses that utilize Kapβ1/Nup98 to gain access to the nucleus include HIV (23), dengue (24), polio (25), and the oncolytic Vesicular Stomatitis virus (VSV) (26) 100.

The viruses Adenovirus, measles, dengue, CMV, HIV and RSV replicate in the nucleus, and exit their genomes into the cytoplasm via the CRM1/Nup98 pathway, which is used by the host cell mainly as means for protein export. VSV 100 replicates in the cytoplasm and directly blocks Rae1/Nup98 cellular mRNA export (11-13, 17), although the disclosure is not bound to a particular modality of operation. Most viruses known to take over NPC transport machinery target, either directly or indirectly, components of Nup98 transport. Nup98 212 is essential for NPC 200 function, and is important for transport of proteins as well as for export of mRNAs (27). Nup98 plays roles in several important biological events such as gene expression, mitotic control and pathogenesis (reviewed in Iwamoto, 2010). Nup98 chromosomal rearrangements have been implicated in many forms of cancer (28). Furthermore, Nup98 is emerging as a new subtype of protein that utilizes autoprocessing to control biogenesis pathways and intracellular translocation. Autoprocessing is a rare biological event, important for protein/antigen processing, G protein-coupled receptor in cell signaling, hypercholesterolemia, and maturation of viral proteins (29).

The class of drugs known as statins, or 3-hydroxy-3-methylglutaryl coenzyme A (HMG-CoA) reductase inhibitors have an ability to effectively lower circulating levels of LDL-cholesterol (LDL-C) (30). Statins affect many metabolic pathways and organ systems, and they may impact several disease states, independently of LDL-C reduction. Such protective non-lipid-lowering effects of statins are referred to as pleiotropic effects. One advantageous pleiotropic effect of statins is disclosed to be an interference with the infectivity and proliferation of viruses. Examples of viruses that are modulated by statins include the human immunodeficiency virus (HIV) (31, 32), influenza (33), poliovirus (34), hepatitis C virus (HCV) (35, 36), hepatitis B virus (HBV) (37), cytomegalovirus (CMV) (38), respiratory syncytial virus (RSV) (39), Dengue (40), measles (41), and adenovirus (42). Statins possess antiviral actions against unrelated viruses, possibly via shared cellular antiviral pathways. Most of the viruses affected by statins may also take-over NPC functions.

Antiviral mechanisms for statins may include: (a) disruption of viral entry due to cholesterol depletion of lipid rafts (34); (b) formation of intracellular vesicles that do not support viral replication (34); (c) inhibition of cellular protein prenylation by lipophilic statins, leading to reduction of viral RNA as well as viral protein synthesis and suppression of virion release (34, 43); and (d) targeting of Rho GTPases, which in turn alter actin cytoskeleton re-arrangements needed for viral entry and budding (31, 32, 44).

The disclosure clarifies that statins can interfere with VSV infection, and can modulate the expression of key nucleoporins, such as Rae1 and Nup98.

Other underlying cellular factors involved in the delicate balance between infected host vs. viral control of cellular functions, are the proteins of antiviral interferon response RAS/Raf/ERK pathway and the human Myxovirus Resistance 1 (MxA). MxA is a powerful antiviral agent against VSV. It is a member of the large dynamin-like Mx protein family, and a large guanosine-5'-triphosphatase (GTPase). MxA can shuttle between the nucleus and the cytoplasm, where it interacts with lipids and forms vesicle-like structures. When overexpressed, it accumulates in distinguishable speck-like nuclear structures known as Nuclear Bodies. Mx proteins are also involved in fundamental cellular processes, such as membrane-associated intracellular vesicle transport (45).

The disclosure advantageously takes an entire-cell approach, and focuses on features that are important for viral infection, replication and cellular defense. A factor needed for viral replication/budding is the cellular membrane, and in particular the integrity of membrane microdomains, or lipid rafts. VSV depends on lipid raft-like structures that interact with viral M protein and promote envelopment of viral particles. Statins also disrupt lipid rafts, therefore, the disclosure exploits the effects of statins and VSV infection on a lipid raft protein marker, Flotillin-1. This marker aggregates on microdomains, and when overexpressed, forms vesicle-like structures in the cytoplasm, which most likely will coincide with sites of high viral activity (46).

The disclosure identifies common features of oncolytic viral infection, replication and cellular defense, and advantageously reveals insights into the mechanisms of statins. The effect of statins upon VSV replication, viral protein expression, and viable progeny was tested, including statins' effects on: (a) levels of nucleoporins Rae1 and Nup98; (b) cellular distribution of mRNA; (c) distribution and levels of lipid raft marker Flotillin-1; (d) levels of signaling proteins ERK1/2 and antiviral MxA. In accordance with the disclosure, it appears that simvastatin exerts effects via the following mechanisms: (1) by modulating the expression and function of key antiviral components of NPC transport, Rae1 and Nup98, simvastatin may counteract the cytopathic effects of VSV; (2) by directly lowering cholesterol on the membrane, and disrupting microdomains, simvastatin may render the cellular membrane more permeable to VSV infection, which in turn, facilitates viral replication and/or budding; and (3) by modulating cellular innate immune proteins, ERK1/2 and MxA, simvastatin may shift the balance of virus vs. host antiviral processes, possibly enabling fast elimination of VSV-infected cells (i.e. increased levels of apoptosis).

Materials and Methods

Cell Culture

HeLa (human cervical adenocarcinoma) cells and BHK-21 cells (Baby Hamster Kidney) cells were obtained from the American Tissue Culture Collection (ATCC Cat. N. CCL-2 and C-13). Cells are grown in DMEM (Cellgro, Fisher Scientific, PA) containing 10% fetal bovine serum (FBS, Fisher Scientific HyClone, PA), supplemented with 1% antibiotic/antimycotic solution (FBS, Fisher Scientific HyClone, PA) in atmosphere of 5% $CO_2$, at 37° C.

Cholesterol Inhibition and Infections

For cholesterol synthesis inhibition studies, HeLa cells were treated with either simvastatin or pravastatin (EMD/Merck, NJ), for the indicated concentrations and time points. HeLa infections with VSV-GFP virus (gift from Dr. Glen Barber, University of Miami Sylvester Cancer Center), were performed as previously described (13). Briefly, HeLa cells were plated in either 100 $mm^2$ plates, or on glass cover slips placed on 6-well plates. At 100% confluency, cells were washed with PBS, and infected with VSV-GFP in low volume DMEM without FBS or antibiotics. Infection proceeded for 1 hr with rocking every 10 minutes. Consequently, the infecting media was removed, and complete media was added. Cells were further incubated for 16 hrs (O/N).

For Cholesterol-sequestering from cellular membranes, we used Methyl-β-Cyclodextrin (MβCD). MβCD, like lipophilic statins, lowered levels of membrane cholesterol and also disrupts microdomains called lipid rafts. HeLa cells were treated with indicated concentrations of MβCD (Sigma-Aldrich, MO) for 45 min. prior to VSV-GFP infection as described above.

Immunoblots

Cells were lysed with the following buffer: 50 mM Tris-HCl (pH 8.0), 150 mM NaCl, 15 mM MgCl2, 0.5% NP40, 0.1 mM Na3V04, 0.1 M NaF, and protease inhibitors cocktail (Sigma-Aldrich, MO). Lysates were kept on ice for 20 min, sonicated, and then centrifuged at 14,000×g for 30 min. Protein concentration was determined by the Lowry Protein Assay Method. Reducing agent and loading buffer with bromophenol blue were added to the samples, and immunoblot analysis was performed. Proteins were separated by 12% SDS-P AGE, and transferred into PVDF membranes (GE healthcare, NJ). Non-specific sites were blocked with 5% milk in PBS/0.05% NP-40 (Sigma-Aldrich, MO). The membranes were incubated with primary antibodies: mouse polyclonal anti-VSV-GFP (gift from Dr. G. Barber, University of Miami Sylvester Cancer Center, FL); rabbit polyclonal anti-Nup98 (gift from Dr. B. Fontoura, University of Texas, Dallas, Tex.); goat polyclonal anti-Rae1 (Abcam, MA); MxA (Santa Cruz Biotechnology, CA); ERK1/2 (Cell Signaling Technology, MA). The membranes were washed with PBS/0.05% NP-40 and incubated with a secondary antibody conjugated to HRP (American Qualex, CA). The VSV protein bands were detected by chemiluminescence using West-Phemto Supersignal Substrate (Thermo-Fisher Scientific, PA). Quantitation of bands was performed using Image-J software program (NIH).

Viral Titer Assay

HeLa cells were treated as described above. After 16 hrs of VSV-GFP infection, a sample of the supernatant was collected and frozen at −80° C. BHK-21 cells were plated into six-well plates and cultured to 80% confluence. Culture medium was removed from each well and replaced with 300 nl of serially diluted viral samples. The inoculated monolayers were left at room temperature for 1 h to allow virus adsorption. The plates were rocked gently every 10 minutes. At the end of the adsorption period, the inoculum was removed from each BHK monolayer and then replaced with 1.5 ml of DMEM 1% Low-Melting-Point agarose (LMPA) (Sigma-Aldrich, MO) in order to immobilize viral plaques. The plates were left at room temperature for an additional 10 minutes in order to solidify the plaque isolation media and then returned to the incubator for 24 h. The LMPA was melted by microwave (10 sec, maximum power) and removed. The BHK-21 monolayers were fixed and stained by the addition of 1 ml of Gentian violet diluted in methanol (0.01% (w/v), Sigma-Aldrich, MO). Particles of Infectitious Units (pfu) were calculated per ml. of supernatant (pfu/ml) of duplicate samples. Data were analyzed using One-way ANOVA (GraphPad Prism5). Statistical significance was determined by p values less than 0.05.

Cell Viability MTT Assays

Cells were seeded at a density of $1 \times 10^{4}$ in 96-well plates. Each of 4 experiments were performed using eight wells per treatment condition. Cells were pretreated with the respective concentrations of cholesterol-lowering drugs, followed by O/N infection with VSV-GFP, as described in the immunoblot protocol. After infection, cells were treated with 5 μg/ml MTT (3-(4,5-Dimethylthiazol-2-yl)-2,5-diphenyltetrazolium bromide (Sigma-Aldrich, MO) and incubated for 4 hrs at 37° C., 5% $CO_2$. MTT is a yellow tetrazole that is reduced to purple formazan by enzymes in living cells. After incubation, the media was aspirated, and the converted dye was solubilized using 200 μl Dimethyl sulfoxide (DMSO) (Sigma-Aldrich, MO) per well. Endpoint absorbance was measured with a plate-reader at wavelength of 570 nm.

Oligo-dT In Situ Hybridization and Confocal Microscopy

Cells were grown on glass coverslips, pretreated with different concentrations of simvastatin for 8 hrs, and then infected with VSV-GFP at MOI of 1.0. After 16 hrs of VSV-GFP infection, in situ hybridization of poly (A) RNA using a biotinylated oligo-dT 45mer was performed, as previously described (13). Briefly, cells were fixed with 4% formaldehyde for 8 min, extensively washed with PBS (3 washes, 15 min each), permeabilized with 0.5% Triton X-100 (Sigma-Aldrich, MO) for 5 min, washed again in PBS (2 washes, 15 min each), then equilibrated in pre-hybridization mix (without oligo-dT) for 20 min at 42° C. in a humidifying chamber placed in a hybridization oven followed by overnight hybridization with biotinylated oligo-dT probes. Hybridization mix was composed of 2×SSC with 1 mg/ml tRNA, 10% dextran sulfate, 25% formamide, and 50 µg/mlbiotinilated-oligo-d (T). After hybridization, samples were washed twice for 15 min with 2×SSC at 42° C. and once for 15 min with 0.5×SSC at 42° C. Cells were fixed with formaldehyde, and washed in PBS as described above. Cells were then incubated with CY5-streptavidin (Jackson Immunoresearch, PA) for 30 min at room temperature. Cells were washed 3× with PBS and stained with Hoescht 33258 (Invitrogen, CA) for 5 min in a humidifying chamber at room temperature. Cells were washed 3× with PBS, then mounted on glass slides using the ProLongGold Antifade reagent (Invitrogen, CA). Samples were examined on a Zeiss LSM510 confocal microscope. Fields of cells representing generalized effects were depicted.

Results

Effects of Simvastatin and Pravastatin on VSV Protein Expression

The effects of statins on VSV infection were studied in HeLa cells exposed to the virus. Cells were pretreated with simvastatin, pravastatin or the statin-vehicle (DMSO) for different times and several drug concentrations. At the end of the statin or statin-vehicle pretreatment, HeLa cells were infected with VSV-GFP for 16 additional hours. Subsequently, the cells were harvested and the supernatants and cell lysates analyzed.

VSV proteins were detected by immunoblot employing anti-VSV-GFP antibodies. Supernatants and cell lysates from VSV-infected cells showed three major bands compatible with G, N/P, and M viral proteins (FIGS. 3A-3C, 4, 5A-5C and 6). Exposure of cells to 0.125 µM simvastatin for 8 h prior to the viral infection increased VSV-protein levels both in supernatants (FIGS. 3A-3C and 4) and cell lysates (FIGS. 5A-5C and 6). Larger percentages of increase above control levels were observed for G and M proteins in supernatants and for N/P viral proteins in cell lysates. Pretreatment of cells with 0.25 µM or higher concentrations of simvastatin decreased VSV protein levels both in supernatants and lysates. With 1 µM or higher concentrations of simvastatin, VSV protein concentrations were reduced to substantially undetectable levels.

Figures 7A, 7B:
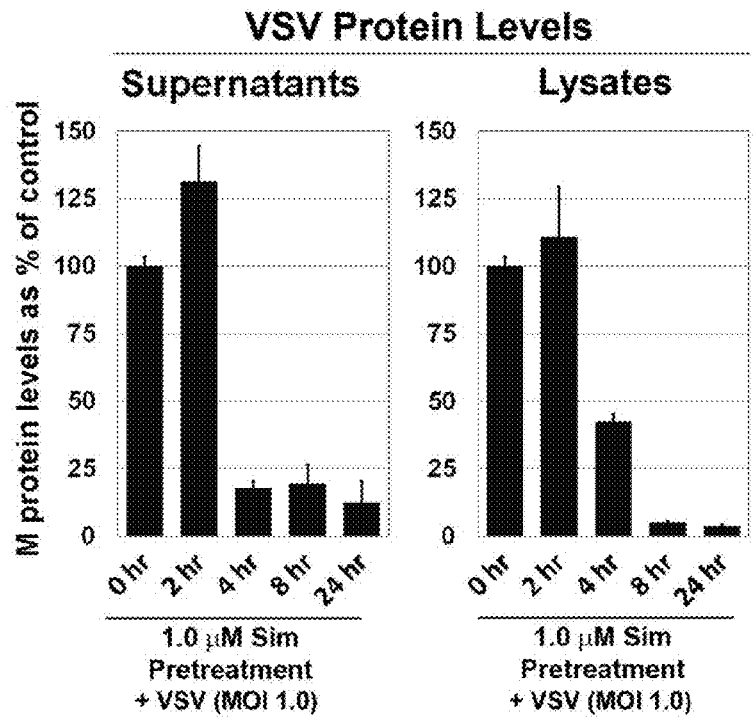
FIGS. 7A-7B illustrate pretreatment time-course and correlation with VSV protein levels. HeLa cells were pre-treated with 1.0 μM simvastatin for time points ranging from 0 hrs to 24 hrs prior to infection with VSV-GFP at MOI of 1.0, for 16 h. Detection of viral proteins are shown by immunoblot assays performed with anti-VSV-GFP antibodies. Plotted are the levels of M protein.

Time of exposure of HeLa cells to simvastatin prior to the VSV infection (pretreatment time) was important in determining the magnitude of the drug effects (FIGS. 7A-7B). Pretreatment times of about 4 hours or longer were required for 1 µM simvastatin to inhibit VSV protein levels; with greater effects at pretreatment times longer than 6 hours (FIGS. 7A-7B).

Pretreatment (2-24 hours) with pravastatin, a non-lipophilic statin with poor cell penetration, failed to alter VSV protein expression at any of the concentrations tested (0.1 to 2.0 µM) (data not shown).

Effects of Methyl-β-Cyclodextrin on VSV Protein Expression

Figure 8:
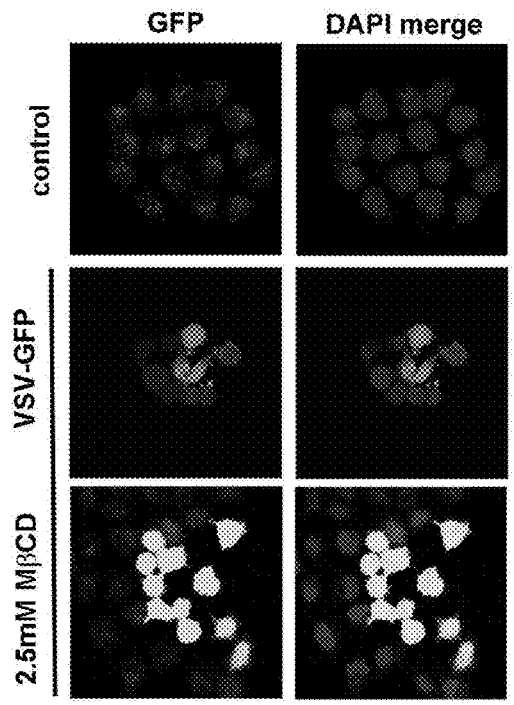
FIG. 8—Confocal imaging showing GFP and nuclei of control cells, VSV-GFP infected cells, and 2.5 mM MβCD pretreated and infected cells.
Figures 11A, 11B, 11C:
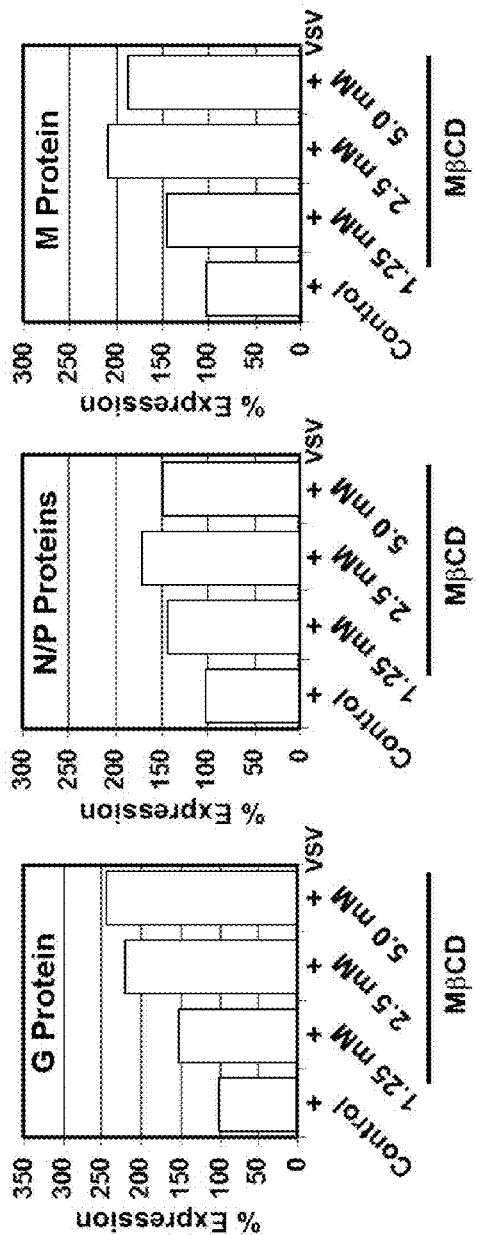
Figure 12:
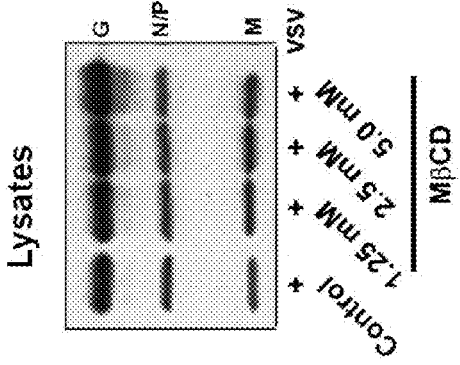

MβCD sequesters cholesterol from the membrane by forming water-soluble complexes. It is also efficient in disrupting membrane microdomains known as lipid rafts. HeLa cells were pretreated with increasing concentrations of MβCD (from 0.125 mM to 5.0 mM) for 45 minutes prior to O/N infection with VSV-GFP at MOI of 1.0. FIGS. 8 and 12 show that the levels of viral protein in both supernatants (FIGS. 9A-9C and 10) and lysates (FIGS. 11A-11C and 12) increased in a MβCD concentration-dependent manner. In supernatants, 1.25 mM MβCD increased protein levels of: G to 150%; N/P to 153%; but M exhibited a relatively small change (105%). 2.5 mM MβCD increased levels of: G to 195%; N/P to 220%;

but M, again was not altered to a great extent (103%). 5.0 mM MβCD increased levels of: G to 182%; N/P to 275%; and M was increased to 125% (FIGS. 9A-9C and 10). In cell lysates, 1.25 mM MβCD increased protein levels of: G to 150%; N/P to 147%; and M to 149%. 2.5 mM MβCD increased levels of: G to 210%; N/P to 162%; and M to 207%. 5.0 mM MβCD increased levels of: G to 247%; N/P to 150%; and M to 180% (FIGS. 11A-11C and 12).

Without being bound to a particular theory, these results suggest that the cholesterol-lowering property of simvastatin may be connected to the stimulation of VSV replication, and not to antiviral effects. FIG. 8 shows high levels of VSV-GFP in cells pretreated with 2.5 mM MβCD and infected as indicated above. Live cell imaging experiments show that viral penetration time was slightly lowered for cells treated with MβCD, as was the case for cells treated with simvastatin (data not shown).

Effects of VSV Infection on Cellular Distribution of Lipid Raft Protein Flotilin-1.

Flotillin-1 is an integral protein that localizes on lipid rafts. When overexpressed, it generates de novo membranes microdomains with lipid raft properties, and induces the formation of dynamic membrane invaginations as well as intracellular vesicles (46). Since simvastatin disrupts lipid rafts, which are important for viral replication, and simultaneously causes vesicle-like formations (FIG. 17), the disclosure details testing of whether VSV and/or simvastatin altered the expression of Flotillin-1, and if this lipid raft protein co-localized with VSV replication sites. If Flotillin-1 coincided with sites of VSV replication, it would probably be incorporated into the envelope structure of the virus, once the particles budded out of the cells, and could therefore be detected on the supernatants.

Indeed, FIGS. 13 and 14A-14B show that VSV infection re-distributed endogenous Flotillin-1 from cytoplasmic/membranous sites (control) to vesicle-like structures near the membrane (VSV-GFP). These vesicle-like structures co-localized to sites of intense viral replication (FIG. 13: arrows show co-localization) Immunoblots from supernatants show that at the low 0.125 μM simvastatin concentration, Flotillin-1 levels increased to ~160% (FIGS. 14A-14B). In this disclosure, the symbol '~' is intended to mean "about". In lysates, it remained close to control levels (~100%). At 0.5 μM simvastatin, supernatant levels decreased to ~75% of control, and lysates decreased to ~90%. Surprisingly, at 2.0 μM simvastatin, supernatant levels decreased to ~40%, while lysate levels increased to ~140% (FIGS. 14A-14B). The high levels of Flotillin-1 on the supernatants corresponding to 0.125 simvastatin suggest that this lipid raft protein is associated with microdomains that stimulate VSV budding. At 2.0 μM simvastatin, Flotillin-1 accumulates intracellularly, and it is possible that this is because VSV proteins are downregulated and therefore the virus can't bud out of the cells, although the disclosure is not intended to be bound to any particular theory.

Effects of Simvastatin and Pravastatin on Viral Titers.

Figure 15:
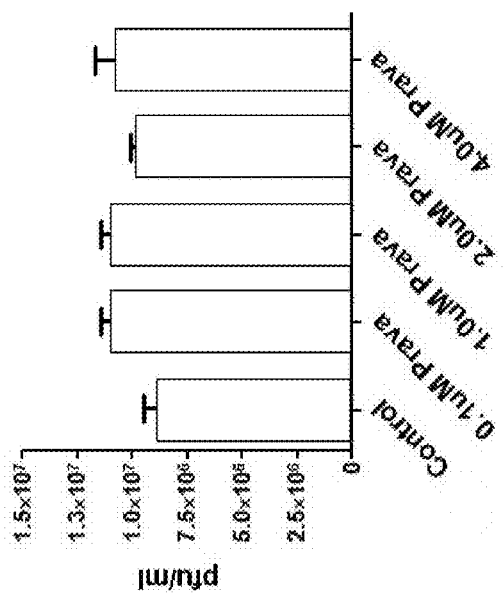
Figure 16:
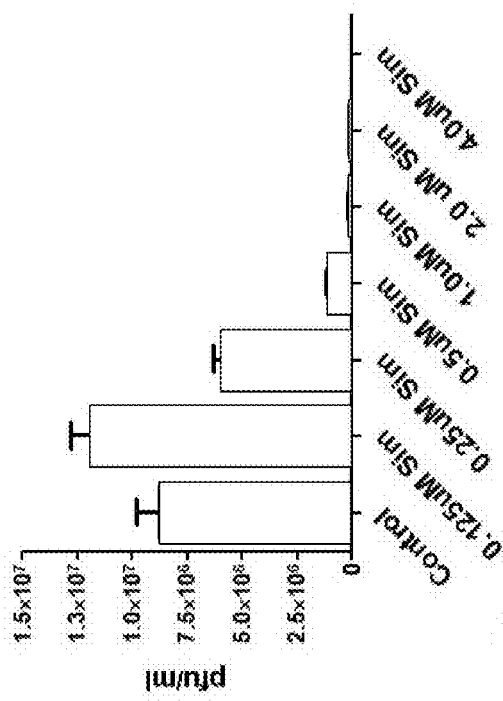

The disclosure details an investigation of whether the effects of simvastatin and MβCD on VSV protein expression correlated with differences in the production of viral titers in supernatants of HeLa cells. In order to measure attenuated production of VSV infectious particles (pfu), viral titer assays were performed of supernatants obtained from either simvastatin, pravastatin, or MβCD pretreated cells that had been infected with VSV-GFP at MOI of 1.0. FIGS. 15-17 show that viral titers were attenuated by different concentrations of simvastatin and MβCD, but not by pravastatin pretreatment.

The average titer value for VSV control infections was of $8.75 \times 10^6$ ($+/-1.05 \times 10^6$) pfu/ml. Concentrations of simvastatin pretreatment ranging from 0.25 μM to 4.0 μM efficiently decreased VSV titers in a dose-dependent response. The simvastatin concentration needed for reduction of pfu values to half of control (IC50) was estimated to 0.278 μM. Pfu values obtained using 4 μM simvastatin pretreatment [$1.80 \times 10^4$ ($+/-3 \times 10^3$) pfu/ml] were 660 fold lower than control pfu counts obtained from non-treated, control VSV-infected cells (FIGS. 15-17), which corresponded to a decrease of 2 log-units (p<0.0001). 5.0 mM MβCD pretreatment decreased VSV titers 160-fold, from $8.3 \times 10^{\wedge}6$ ($+/-1.4 \times 10^{\wedge}6$) to $5.25 \times 10^{\wedge}4$ ($+/1-5.5 \times 10^{\wedge}3$). This decrease is significant, however, MβCD is highly toxic to HeLa cells, and overall viability was low, not allowing a true assessment of drug antiviral activity via titering. Another statin tested, lovastatin, presented results of cell toxicity similar to MβCD (data not shown).

Viability of HeLa Cells after Statins or MβCD Treatment and Viral Infection.

The disclosure further details an investigation of whether the antiviral effects were true drug effects on viral replication, or were artifacts due to cell toxicity and decreased viability. Overall, the experimental conditions were designed to maximize drug effects on the virus, and minimize cell killing. Cells were reasonably tolerant of the combined treatment of simvastatin, as well as pravastatin, and viral infection. FIG. 18 showed that simvastatin treatment alone caused slight dose-dependent reductions in cell viability. Pattern analysis of cell death rate (Δ% cell death) over units of drug concentration (ΔμM simvastatin) indicated that treated, but uninfected cells were dying at a rate of −1.63% cells/μM Sim (FIG. 18, slope "a"). In comparison, cells that were infected, but not treated with simvastatin, showed ~20% less survival (FIG. 18). Cells that were pretreated with simvastatin and infected, showed an accelerated rate of cell death corresponding to −2.61% cells/μM Sim, indicating a synergistic effect of simvastatin and VSV on cell killing (FIG. 18, slope "b").

Treatment of cells with pravastatin also caused decreased cell survival as a function of drug concentration, with cell death rates of −1.78% cells/μM Prava (FIG. 19, slope "c'). However, when cells were pretreated with pravastatin and infected, the rates of cell death were lowered to −1.20% cells/μM Prava (FIG. 19, slope "d'). The relatively low toxicity of simvastatin and pravastatin support the observation that the effects on viral replication are not artifacts due to increased cell death.

Lovastatin, as well as MβCD were highly toxic to HeLa cells, showing cell survival at ~20% for 5 mM MβCD and ~30% for 3 μM lovastatin (FIGS. 20-21).

Pre-Treatment of Simvastatin Reverts VSV-Mediated Inhibition of mRNA Export.

Figure 22:
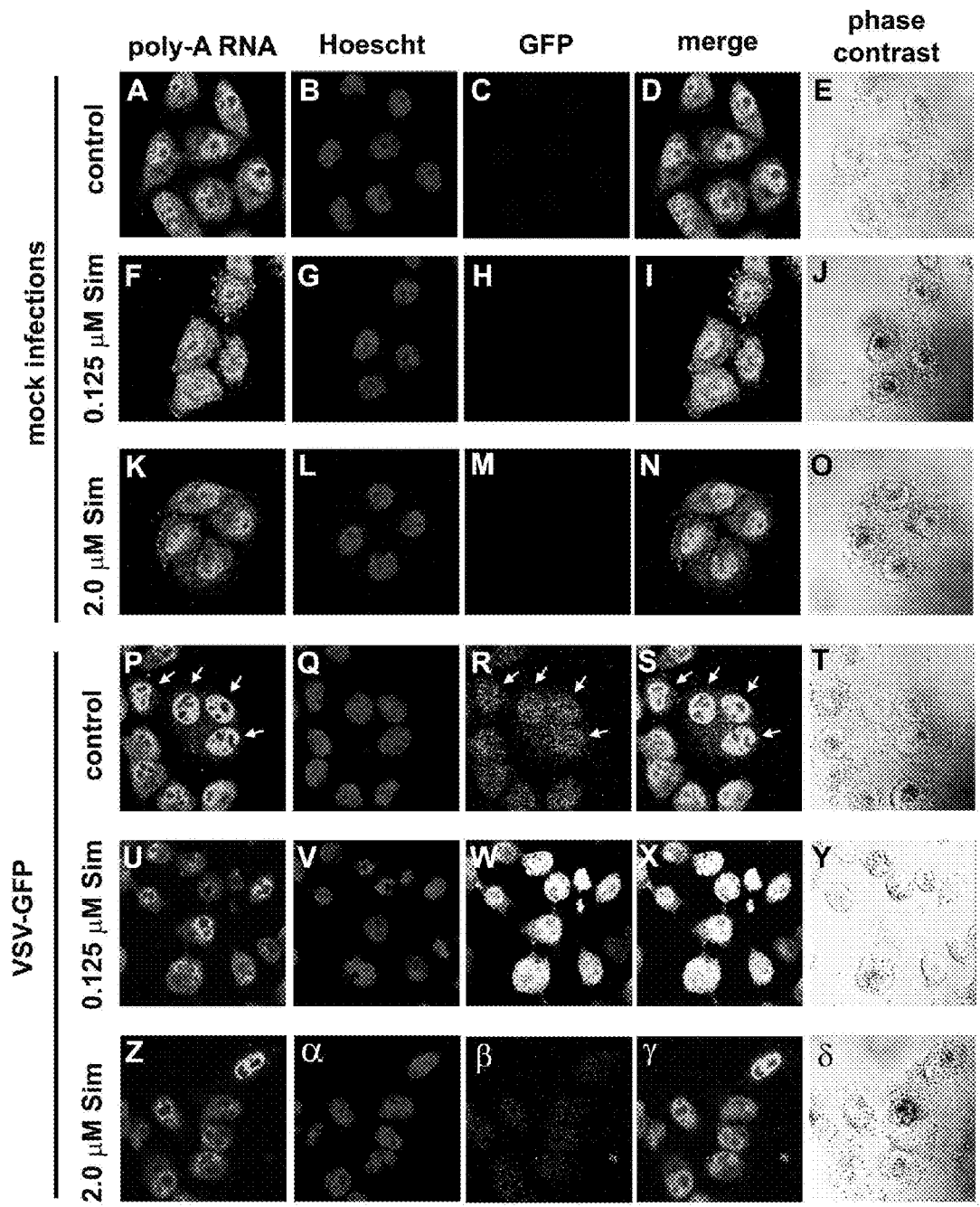
FIG. 22 illustrates VSV Infection inducing mRNA export block that is reversed by simvastatin treatment. Oligo-dT in situ hybridization and GFP autofluorescence were performed to detect poly(A) RNA and VSV-GFP, respectively. Cells were pretreated (or not) with simvastatin at the indicated concentrations for 24 h, then infected with VSV-GFP at MOI of 1.0. Non-infected cells (mock-infections) show the effects of simvastatin on mormal distribution of poly(A) RNA (panels A-O). Control VSV infection shows typical nuclear retention of poly(A) RNA (panels P-T). Cells pretreated with 0.125 μM Sim show partial recovery from mRNA block (panel U) and a remarcable increase in GFP fluorescence (panel W). The same condition also shows cytophatic morphological changes in the infected cells (panel Y). Cells pretreated with 2.0 μM Sim show near complete recovery from mRNA nuclear block (panels Z-γ), and normal distribution of poly(A) RNA between the nucleus and the cytoplasm (panel Z). This condition also shows recovery of cell morphology (panel δ). Samples were examined by confocal microscopy.

In accordance with the disclosure, VSV causes blockage of mRNA nuclear export. In order to visualize the mRNA distribution in situ, a hybridization of mRNAs poly-A tails using oligo-dT 40-mer probes was performed. FIG. 22, Panel A illustrates the normal distribution of mRNA in HeLa cells. Notice that mRNA is present in the nucleus and in the cytoplasm of each cell. The nuclei (FIG. 22, Panel B) were stained with Hoescht dye, to indicate the location of the nuclei and that all cells present on the slide were hybridized with the mRNA probe. Merging both stains reveals the detailed distribution of mRNA across the cells (FIG. 22, Panel D). Phase contrast images (FIG. 22, Panel E) allow for comparison of general cellular morphology as pertaining to each treatment condition. Control VSV-infected cells (FIG. 22, Panel P) showed a typical accumulation of mRNA at nuclear sites (VSV-GFP control infections, panels P-S, white arrows).

In order to observe the effects of simvastatin on mRNA distribution, non-infected cells (mock infections) were treated with either 0.125 μM or 2.0 μM of the drug. Simvastatin treated cells showed a more pronounced mRNA cytoplasmic distribution than mock untreated cells (FIG. 22, compare panels A, F and K). Also, simvastatin treatment caused the emergence of mRNA-containing, vesicle-like structures in the cytoplasm of HeLa cells (FIG. 22, Panels F and K).

Compared to control VSV infections, Hela pretreatment of 0.125 μM simvastatin partially reversed the viral mRNA export block (FIG. 22, Panel U). This may be observed, for example in the presence of cells showing normal distribution of mRNA between the nucleus and the cytoplasm, as well as cells showing retention of mRNA in the nuclei (FIG. 22, Panel U). An interesting phenotype observed with 0.125 μM simvastatin pretreatment was the high intensity of GFP expression present in most infected cells (FIG. 22, Panel W). The degree of overexpression was considerably higher than for control VSV infections (FIG. 22, comparing Panels R and W), therefore the original detection acquisition signal for confocal laser wavelength of 488 nm became saturated. In order to avoid pixel-saturation, the image acquisition pertaining to this condition was lowered to 40% of the original values. The high intensity of the 488 nm channel indicated high levels of viral GFP protein expression, and therefore high levels of VSV. These results corroborate the immunoblot data in FIG. 6, lane 3, which quantitatively showed higher expression levels of viral proteins. Furthermore, several infected cells showed cell rounding and either fragmented or enlarged nuclei, indicating high incidence of apoptosis. Also observed with this pretreatment condition, was the deteriorated morphology of infected cells (FIG. 22, Panel Y), when compared to normal morphology of control cells (FIG. 22, Panels E, J, O).

Pretreatment with 2 μM simvastatin induced recovery from viral mRNA export block, which was indicated by the normal distribution of mRNA between the nucleus and the cytoplasm of infected cells (FIG. 22, Panels Z-γ). Also depicted in FIG. 22, panel Z, is a cell on the upper right corner that showed a characteristic VSV nuclear block of mRNA (saturated nucleus), indicating the distinguishable presence of the virus, although the conventional detection of VSV presence (GFP) was very faint (FIG. 22, Panel β).

These results coincided with immunoblot data shown in FIG. 6, lane 6, where viral proteins could barely be detected. In addition, most of the cells pretreated with 2.0 μM simvastatin, showed recovery from morphologic cytopathic effects (FIG. 22, Panel 6).

Simvastatin Upregulates NPC Antiviral Proteins Rae1 and Nup98.

It has been shown that Rae1 is the binding target of VSV M protein (13). Upregulation of Nup98 and/or Rae1 either by interferon treatment or by ectopic expression reverts the mRNA export block mediated by VSV M protein (13, 17). This effect indicates that both Rae1 and Nup98/Nup96 genes are involved in antiviral response. These findings are further supported by the fact that both Rae1 and Nup98 are upregulated by interferon (13, 17). Low concentrations of simvastatin (0.01-1 µM) are known to upregulate interferon-γ (47), and since simvastatin pretreatment presented a distinguished anti-VSV effect, the disclosure tests whether simvastatin could alter the expression levels of Rae1 and/or Nup98. As shown in FIGS. 23-24, simvastatin increased both Nup98 (98 KDa) and Rae1 (42 KDa) protein levels in a dose-dependent manner. At treatment condition of 0.125 µM for 24 hrs, Nup98 protein level increased to 180%, while Rae1 increased to 196% of control expressions, arbitrarily set as 100%. At 0.5 µM simvastatin treatment, Nup98 increased to 240%, and Rae1 increased to 310% of control values. Recalling results from FIG. 3A-3C, 0.5 µM simvastatin treatment exerted a pronounced antiviral effect towards VSV. At treatment conditions of 2.0 µM, we have observed the largest increase in both Nup98 to 260%, and Rae1 to 390% of control levels. These substantial increases in anti-VSV proteins expression supported the results obtained for reversal of mRNA export block (FIG. 22).

Simvastatin Modulates the Expression of Key Proteins Involved in VSV Replication: MxA and ERK1/2.

It is known that in approximately 30% of cancers, RAS/Raf/ERK pathway is upregulated (48). Importantly, these cancers do not respond to conventional therapeutics (49). Cancer cells that have RAS/Raf/ERK pathway upregulated, do not induce MxA protein, which is a powerful antiviral agent, and therefore favor the replication of viruses, such as VSV. Here we have shown that, in accordance with studies by He et al. (50), simvastatin exerted a biphasic action upon ERK protein regulation: at low simvastatin concentrations, ERK protein was upregulated. At higher concentrations, ERK levels fell. Further investigating the levels of MxA, protein levels were increased to ~400%, 650%, and 150% when pretreated with simvastatin at 0.125, 0.5, and 2.0 µM, respectively (FIG. 25-26).

Discussion

The disclosure describes four exemplary novel pleiotropic properties of simvastatin:

(1) Simvastatin caused a biphasic, concentration-dependent effect towards modulation of VSV infection and replication. At low concentration (0.125 µM), simvastatin promoted high levels of viral protein expression and replication, which may be due to cholesterol depletion, since MβCD produced similar results. At subsequent higher concentrations (from 0.25 to 2.0 µM), simvastatin inhibited VSV proteins expression and viral replication. This antiviral activity may have been mediated by effects of simvastatin on host cell gene expression levels. Supporting this deduction is the fact that cells needed to be incubated with simvastatin for at least 4 hrs prior to VSV infection in order for changes in viral content to be observed.

(2) Simvastatin modulated endogenous mRNA distribution by upregulating mRNA export factors Rae1 and Nup98, which also possess antiviral properties.

(3) Simvastatin upregulated antiviral protein MxA via modulation of IFN-inducible RAS/Raf/ERK pathway.

(4) Simvastatin redistributed lipid raft marker protein flotillin-1, which co-localized with high replication sites of VSV.

The results disclosed for the biphasic effects of simvastatin differed from experiments by Delang et al, who had tested the pleiotropic properties of simvastatin against several viruses, including VSV. Delang's group had simultaneously conducted simvastatin treatment and viral infections on cells, therefore not observing the drug's effects towards the tested viruses (35). Another observation that supports simvastatin's pretreatment time requirement is the fact that VSV blocks host gene expression within 2 hrs of infection by inhibiting Rae1/Nup98 cellular mRNA export. Therefore, if cells are simultaneously treated with statins and infected, one should expect not to observe innate antiviral effects in vitro, since cellular responses via transcriptional/translational upregulation is blocked by the viral matrix protein.

The disclosed data suggest that simvastatin, at low concentration, favors the VSV take-over of cellular translational mechanisms, and simultaneously enhance the budding ability of newly formed progeny. These results are most likely derived from an immediate decrease in intracellular as well as membranous cholesterol levels, as supported by experiments using MβCD. Significantly, expression levels of N and P proteins are known to control viral phase-switch from transcription/translation to genome replication. The increases in N/P protein levels observed with 0.125 mM simvastatin and with MβCD treatment, indicated that VSV was able to replicate more efficiently under those conditions. Thus, it is feasible to infer that cholesterol depletion favors the initial phase of VSV's life cycle, causing a delay of phase-switch from transcription/translation to genome replication. This delay allows for a greater degree of VSV protein expression, as observed.

A non-lipophilic statin drug, pravastatin had previously been shown not to possess antiviral activity against several viruses, including Hepatitis C (HCV) (51), Human Immunodeficiency Virus (HIV) (52), and oncolytic Adenovirus (AdV) (42, 51, 52).

It is becoming increasingly aparent that most viruses favor their own replication by hijacking basic nuclear membrane functions. Since host gene expression is compartmentalized, and all mRNA need to be exported to the cytoplasm in order to be expressed into protein, the gateways to the nucleus (NPCs) become vulnerable targets to viral attack. Recal that the antiviral Nup Rae1 is the target of VSV M protein, and a major factor that mediates mRNA export from the nucleus via Nup98. In the instant disclosure, for the first time, it is shown that statins interfere with the fundamental cellular function of mRNA export by upregulating nucleoporins Rae1 and Nup98, which are in turn, capable of exerting antiviral activity.

The ultimate goal of anti-viral therapy is to completely restore all functions to the infected cells. This goal is currently unattainable, since irreversible cellular damage occurs very early in most viral infections. A more realistic goal for antiviral therapy, and for the prevention of healthy cells, is to inhibit virus replication and/or the spread of viruses to healthy cells. In order to achieve this level of protection, it is important to take in consideration the cellular first line of defense against viral infections: interferon. IFN signaling promotes the activation of innate immune response by synthesizing antiviral proteins, such as nucleoporins Nup98 and Rae1, and proteins of RAS/Raf/ERK signaling pathway, ERK1/2 and MxA.

As mentioned, VSV preferentially replicates in the cytoplasm of cancer cells due to these cells' flaws in IFN innate immunity/antiviral response. The mechanism responsible for the cancer-cell enhanced replication involves constitutive activation of the RAS/Raf/ERK pathway (8). Previously, a study on statins pleiotropic effects have also shown a biphasic dose-related action of the drug on RAS/Raf/ERK signaling pathway (53). Medina et al demonstrated that low concentrations of simvastatin (0.01-0.1 µM) significantly promoted cell proliferation via upregulation of RAS/Raf/ERK pathway, while higher concentrations (>1.0 µM) halted proliferation and induced cell death via downregulation of the same pathway. In accordance with the disclosure, observations of simvastatin biphasic response, and the knowledge that modulation of antiviral MxA expression is also dependent on the RAS/Raf/ERK pathway, the profiles of both ERK1/2 and MxA proteins after simvastatin treatment are studied. The disclosure shows that low concentration of simvastatin pretreatment correlate to an increase in the levels of VSV detected. Furthermore, cancer cells that present aberrant cell division due to RAS/Raf/ERK constitutive upregulation, can be synergistically suppressed by strategic drug combinations of specific inhibitors of the RAS/Raf/ERK pathway, as for example the experimental drug PLX4032 (54), with simvastatin pretreatment followed by oncolytic VSV infection.

Another mechanism of simvastatin anti-VSV action might be related to disruptions of membrane microdomains. We have shown that when cells are infected with VSV, endogenous lipid raft protein Flotillin-1 is re-distributed from a uniform distribution to concentrated vesicle-like structures near the cellular membrane. These vesicle-like structures colocalized with sites of high VSV replication. The observed shift in flotillin-1 distribution pattern, with subsequent accumulation of this lipid raft protein on cell lysates, indicates that simvastatin caused cytoplasmic trapping and a dysfunction of viral budding.

The disclosure applies principles of viral-host interactions in order to investigate the effects of simvastatin on overall VSV replication and on possible antiviral cytoprotection. A multi-dimensional approach has been applied in order to uncover converging cellular factors that are affected by statin treatment. In accordance with the disclosure, it may be advantageous to use simvastatin as a non-specific, or broad-range antiviral agent capable of regulating host cell antiviral proteins, rather than directly interacting with viral components. Furthermore, since simvastatin can potentially either enhance or eliminate VSV infection in a dose-dependent manner, studies in accordance with the disclosure suggest that the drug may advantageously be used as a priming therapeutic neoadjuvant for oncolysis via replication-competent VSV. The disclosure provides insight into novel strategies for the use of statin drugs as both broad-range antiviral agents and oncolytic adjuvants, thereby broadening perspectives towards novel antiviral and anticancer therapies.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method for virotherapy of cancer in which a statin is used to modulate viral replication of an oncolytic virus, the method comprising:

administering a statin to cancer cells of a patient in an amount including a concentration of between about 0.01 and about 0.175 μM of the statin; and infecting the cancer cells of the patient with an oncolytic virus at a time between 2 and 24 hours after administering the statin;

wherein the statin modulates the oncolytic viral replication, thereby enhancing growth of the oncolytic virus and its associated oncolysis at lower concentrations of the statin.

2. The method according to claim 1, wherein the statin is simvastatin (Sim) and the oncolytic virus is Vesicular Stomatitis Virus (VSV).

3. The method according to claim 2, wherein Sim acts to modulate Vesicular Stomatitis Virus (VSV) replication by upregulating nuclear pore complex antiviral factors.

4. The method according to claim 3, wherein the nuclear pore complex antiviral factors are Rae1 and Nup98 proteins.

5. The method according to claim 2, wherein the concentration of simvastatin (Sim) administered is 0.125 μM.

6. The method according to claim 2, wherein infection of the cancer cells is at a Multiplicity of Infection of about 0.01 to 2.0.

7. The method according to claim 2, wherein infection of the cancer cells is at a Multiplicity of Infection of about 1.0.

8. The method according to claim 2, further comprising a second administration of simvastatin (Sim) to the cancer cells of the patient at a higher dosage, whereby the higher dosage of simvastatin (Sim) exhibits an antiviral effect on the Vesicular Stomatitis Virus (VSV).

9. The method according to claim 6, wherein the higher dosage is about 0.25 μM or higher.

10. The method according to claim 2, further comprising administering a different anti-cancer therapeutic substance after administering simvastatin (Sim).

11. The method according to claim 10, wherein the different anti-cancer therapeutic substance is an inhibitor of a RAS/Raf/ERK pathway.

12. The method according to claim 10, wherein the different anti-cancer therapeutic substance is administered at least about 4 hours after the simvastatin (Sim).

13. The method according to claim 10, wherein the different anti-cancer therapeutic substance is PLX4032.

14. A method of combination cancer treatment therapy for a patient in need of cancer treatment therapy, the method comprising:

administering simvastatin (Sim) to the patient in an amount including a concentration of between about 0.01 and about 0.175 μM Sim; and administering an effective amount of Vesicular Stomatitis Virus (VSV) to the patient;

wherein the effective amount of Sim and the effective amount of VSV act in combination to synergistically enhance cancer cell apoptosis, thereby treating cancer in the patient.

15. The method according to claim 14, wherein administering simvastatin (Sim) includes administering the Sim at a time point between 2 hours and 24 hours prior to administering the Vesicular Stomatitis Virus (VSV).

16. The method according to claim 14, wherein Sim acts to modulate Vesicular Stomatitis Virus (VSV) replication by upregulating nuclear pore complex antiviral factors.

17. The method according to claim 16, wherein the nuclear pore complex antiviral factors are Rae1 and Nup98 proteins.

18. A method for virotherapy of cancer in which simvastatin (Sim) is used to modulate Vesicular Stomatitis Virus (VSV), the method comprising:

administering simvastatin (Sim) to cancer cells of a patient in an amount including a concentration of between about 0.01 and about 0.175 µM of Sim;

infecting the cancer cells of the patient with Vesicular Stomatitis Virus (VSV) at a time between 2 and 24 hours after administering Sim, wherein Sim modulates VSV replication, thereby enhancing growth of VSV and its associated oncolysis; and administering a second, higher dosage of Sim to the cancer cells of the patient in an amount including a concentration of about 0.25 µM or higher of Sim, whereby the second, higher dosage of Sim modulates VSV by antiviral effect.

19. The method according to claim 18, wherein Sim acts to modulate Vesicular Stomatitis Virus (VSV) replication by upregulating nuclear pore complex antiviral factors.

20. The method according to claim 19, wherein the nuclear pore complex antiviral factors are Rae1 and Nup98 proteins.

21. The method according to claim 18, wherein the time for infecting the cancer cells of the patient with Vesicular Stomatitis Virus (VSV) is at least 4 hours after administering simvastatin (Sim).

* * * * *